(12) United States Patent
Coffman et al.

(10) Patent No.: US 10,435,670 B2
(45) Date of Patent: *Oct. 8, 2019

(54) METHODS, APPARATUSES, AND SYSTEMS FOR CONTINUOUSLY INACTIVATING A VIRUS DURING MANUFACTURE OF A BIOLOGICAL PRODUCT

(71) Applicant: Boehringer Ingelheim International GmbH, Ingelheim am Rhein (DE)

(72) Inventors: Jonathan Coffman, Union City, CA (US); Jeff Goby, Fremont, CA (US); Scott Godfrey, Pleasanton, CT (US); Raquel Orozco, El Cerrito, CA (US); Jens Holger Vogel, El Cerrito, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 332 days.

This patent is subject to a terminal disclaimer.

(21) Appl. No.: 15/303,776

(22) PCT Filed: Apr. 15, 2015

(86) PCT No.: PCT/EP2015/058172
§ 371 (c)(1),
(2) Date: Oct. 13, 2016

(87) PCT Pub. No.: WO2015/158776
PCT Pub. Date: Oct. 22, 2015

(65) Prior Publication Data
US 2017/0037381 A1  Feb. 9, 2017

Related U.S. Application Data

(60) Provisional application No. 61/979,731, filed on Apr. 15, 2014.

(51) Int. Cl.
*C12N 7/04* (2006.01)
*A61L 2/00* (2006.01)
(Continued)

(52) U.S. Cl.
CPC .............. *C12N 7/00* (2013.01); *A61L 2/0082* (2013.01); *C07K 1/14* (2013.01); *C07K 1/16* (2013.01);
(Continued)

(58) Field of Classification Search
CPC ............ C12N 7/04; A61L 2/0082; C07K 1/14
See application file for complete search history.

(56) References Cited

U.S. PATENT DOCUMENTS

| 5,429,746 A | 7/1995 | Shadle et al. |
| 6,464,936 B1 * | 10/2002 | Mowat ................. A61L 2/0011 250/438 |

(Continued)

FOREIGN PATENT DOCUMENTS

| EP | 1454638 | 9/2004 |
| EP | 2089065 | 5/2008 |

(Continued)

OTHER PUBLICATIONS

International Seach Report for PCT/EP2015/058172 dated Apr. 15, 2015.
"Triton X-100" Wikipedia, viewed May 1, 2019, 3 pgs.

Primary Examiner — Kevin Joyner
(74) Attorney, Agent, or Firm — Atabak R. Royaee

(57) ABSTRACT

Methods for continuously inactivating virus during manufacture of a biological product are provided. The methods include steps of (1) combining (a) a composition including a biological product, and (b) a composition including a virus-inactivation reagent, to obtain (c) a treatment composition having a predetermined property for inactivation of a (Continued)

virus, (2) confirming that the treatment composition exhibits the predetermined property, (3) transferring the treatment composition to a treatment vessel that includes an inlet, an outlet, and a static mixer, the transferring occurring at the inlet, (4) incubating the treatment composition in the treatment vessel at a predetermined temperature while the treatment composition flows at a predetermined rate and contacts the static mixer, and (5) collecting the treatment composition from the treatment vessel at the outlet, w

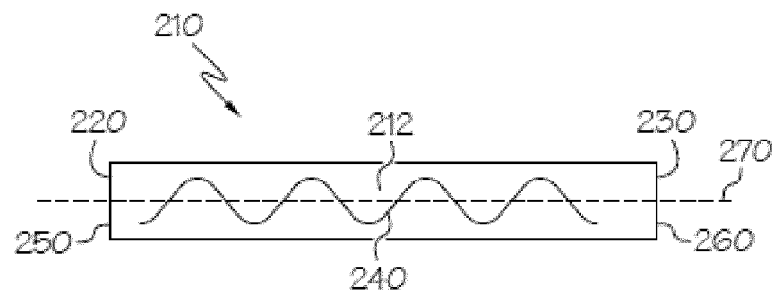
FIG. 2
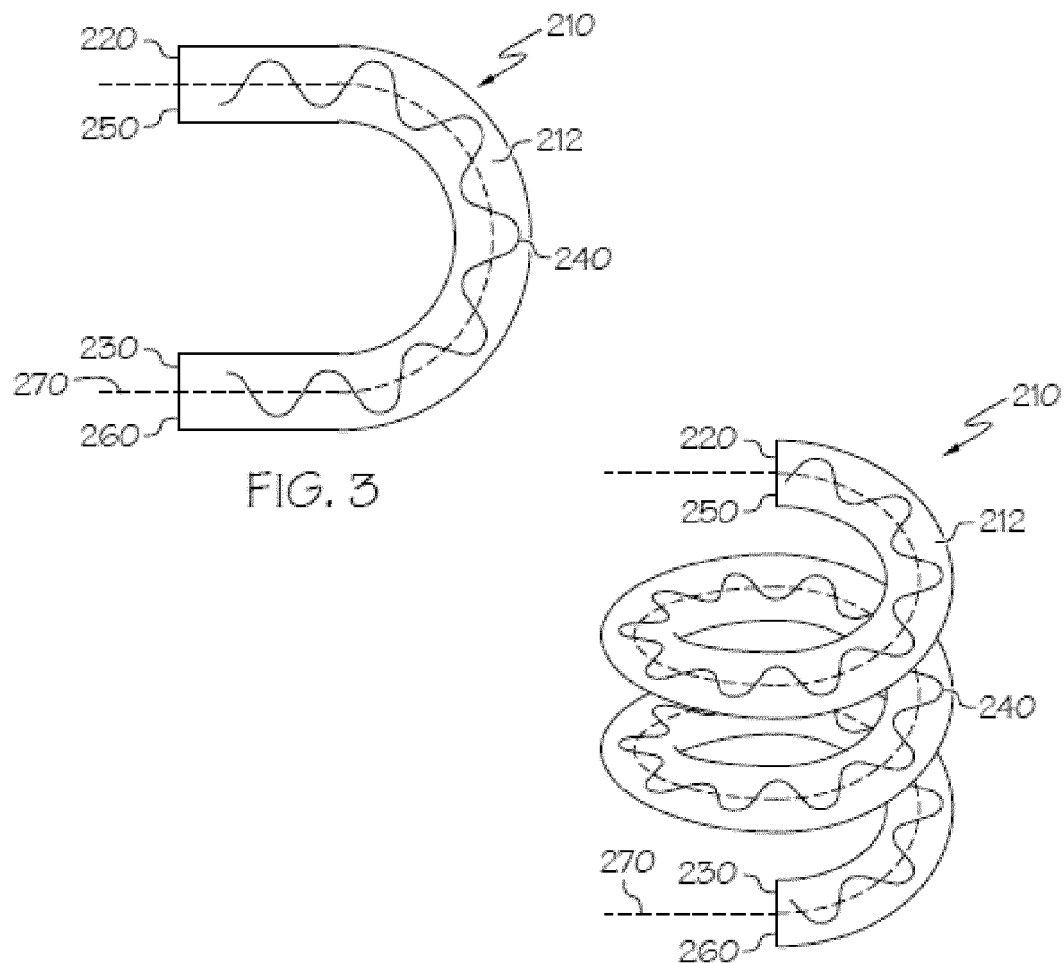
FIG. 3
FIG. 4

METHODS, APPARATUSES, AND SYSTEMS FOR CONTINUOUSLY INACTIVATING A VIRUS DURING MANUFACTURE OF A BIOLOGICAL PRODUCT

RELATED APPLICATIONS

This application is a U.S. National Phase of International Application No. PCT/EP2015/058172, filed Apr. 15, 2015, which claims the priority benefit of U.S. Provisional Application No. 61/979,731, filed Apr. 15, 2014. The entire content of each of the above applications is incorporated herein by reference in its entirety as though fully set forth herein.

FIELD OF THE INVENTION

The present invention relates generally to methods, apparatuses, and systems for continuously inactivating a virus during manufacture of a biological product, and more particularly, to such methods including steps of (1) combining (a) a composition including a biological product, and (b) a composition including a virus-inactivation reagent, to obtain (c) a treatment composition having a predetermined property for inactivation of a virus, (2) confirming that the treatment composition exhibits the property, (3) transferring the treatment composition to a treatment vessel that includes an inlet, an outlet, and a static mixer, the transferring occurring at the inlet, (4) incubating the treatment composition in the treatment vessel at a predetermined temperature while the treatment composition flows at a predetermined rate and contacts the static mixer, and (5) collecting the treatment composition from the treatment vessel at the outlet, wherein steps (1) to (5) are carried out continuously, as well as apparatuses and systems including such a treatment vessel.

BACKGROUND OF THE INVENTION

Inactivation of viruses that may be present in a composition including a biological product that is intended for use in a biopharmaceutical product, such as a therapeutic drug or a vaccine, is an important aspect of quality control for ensuring that the biopharmaceutical product will work as intended and will not inadvertently cause disease or other harm. Viral contamination can occur during the production of a biological product, through both exogenous and endogenous sources. Viruses can be difficult to detect, given the diversity of their structures and genomes, and, once present, can be difficult to physically remove due to their small size. To account for the possibility of viral contamination, industrial processes for production of biological products typically include one or more steps for inactivation of potential viral contaminants.

Typical methods from the state of the art include adding a viral-inactivation reagent, such as an acid or a detergent, to a composition including a biological product, mixing thoroughly, incubating for a specific time, then neutralizing or removing the viral-inactivation reagent, all done in a discontinuous mode, i.e. batch mode, to accomplish inactivation of viruses that may be present in the composition including the biological product, as taught, for example by Ristol Debart et al., U.S. Pat. No. 6,875,848, Shadle et al., U.S. Pat. No. 5,429,746, and Latham et al, U.S. Pub. No. 2013/0236358. In accordance with such methods, inactivation of the viruses that may be present may require multiple discontinuous steps and/or extended incubation times, though, during which time the composition including the biological product typically is not otherwise processed, potentially adding substantial time to the overall process for manufacturing the biological product.

Other methods include treating a composition including a biological product with a dose of light, such as monochromatic or polychromatic light, in a continuous mode, e.g. as the composition flows through a thin-layer irradiator, optionally with mixing to narrow residence time distribution and increase inactivation rate, in order to accomplish inactivation of microorganisms that may be present in the composition, as taught, for example, by Anderle et al., U.S. Pat. No. 7,993,580. Control of the dose of light may be difficult, though, as the dose can vary across the composition depending on factors such as micro-heterogeneities in absorbance and rate of flow of the composition during irradiation, and can vary across time depending on aging of corresponding light sources and fluctuations in light emissions. Other methods include mixing a composition including a biological product with a viral-inactivation reagent, such as an acid or a detergent, continuously, e.g. using one or more in-line static mixers, during flow from a first unit operation to a second unit operation, in order to inactivate viruses that may be present in the composition, with residence time for virus inactivation being altered by having tubes of appropriate diameter and length after each static mixer and before a pH probe, as taught, for example, by Xenopoulos, WO2014/004103. Altering residence time for virus inactivation based on varying diameters and lengths of tubes after each static mixer and before a pH probe may require extensive empirical analysis and/or detrimentally long times of exposure of the biological product to the viral-inactivation reagent, though, given that patterns of flow of compositions in tubes may vary in ways that are complicated and difficult to predict, depending on specific properties of the compositions and dimensions of the tubes, and that patterns of flow of compositions in tubes can still exhibit heterogeneities notwithstanding thorough mixing of the compositions prior to flow of the compositions through the tubes, particularly in the context of scaling up a method for purposes of manufacturing.

Accordingly, a need exists for improved methods for continuously inactivating a virus during manufacture of a biological product, as well as for apparatuses providing treatment vessels specific for such methods.

BRIEF SUMMARY OF THE INVENTION

In a first aspect of the disclosure, a method for continuously inactivating a virus during manufacture of a biological product is provided. The method includes a step (1) of combining (a) a composition including a biological product, and (b) a composition including a virus-inactivation reagent, to obtain (c) a treatment composition having a predetermined property for inactivation of a virus. The method also includes a step (2) of confirming that the treatment composition exhibits the predetermined property. The method also includes a step (3) of transferring the treatment composition to a treatment vessel that includes an inlet, an outlet, and a static mixer and having an internal volume, the inlet and the outlet being positioned at opposite ends of a major axis of the treatment vessel and the static mixer being internal to the treatment vessel along the major axis, and the transferring occurring at the inlet. The method also includes a step (4) of incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property. The method also includes a step (5) of collecting the treatment composition from the treatment vessel at the outlet. In accordance with the method, steps (1) to (5) are carried out continuously. Without wishing to be bound by this theory it is assumed that especially the arrangement of the static mixer being an internal part of the treatment vessel allows an improved interaction of the virus-inactivating reagent with the composition including a biological product and thus improves the activity of the reagent used for the virus-inactivation.

In an example of the first aspect, the predetermined property of the treatment composition includes at least one of (a) a pH between 3.0 to 3.8 or (b) a detergent concentration between 0.05% and 10% (v/v).

In another example of the first aspect, the virus-inactivation reagent includes at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm.

For example, the virus-inactivation reagent can be an acid having a titratable group having a pKa between 2.3 to 4.2 and not having another titratable group having a pKa between 4.2 and 8.5 selected from the group consisting of an organic acid having a titratable group having a pKa between 2.3 to 4.2 and not having another titratable group having a pKa between 4.2 and 8.5, lactic acid, formic acid, ascorbic acid, an amino acid having a titratable group having a pKa between 2.3 to 4.2 and not having another titratable group having a pKa between 4.2 and 8.5, glycine, or a combination thereof.

For example, the virus-inactivation reagent can be an organic acid having a titratable group having a pKa between 2.3 to 4.2 and not having another titratable group having a pKa between 4.2 and 8.5, lactic acid, formic acid, ascorbic acid, or a combination thereof, and the predetermined property of the treatment composition can include a pH between 3.0 to 3.8. In accordance with this example, the confirming of step (2) can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be an amino acid having a titratable group having a pKa between 2.3 to 4.2 and not having another titratable group having a pKa between 4.2 and 8.5, glycine, or a combination thereof, and the predetermined property of the treatment composition can include a pH between 3.0 to 3.8. In accordance with this example, the confirming of step (2) can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be a non-ionic detergent having a chromophoric group having an absorption peak between 230 nm and 600 nm selected from the group consisting of a polyethylene oxide detergent having an aromatic group, Triton-X 100 detergent, and combinations thereof.

For example, the virus-inactivation reagent can be a polyethylene oxide detergent having an aromatic group, Triton-X 100 detergent, or a combination thereof, and the predetermined property of the treatment composition can include a detergent concentration between 0.05% and 10% (v/v). In accordance with this example, the confirming of step (2) can include measuring ultraviolet absorption of the treatment composition, wherein the ultraviolet absorption indicates the concentration of the detergent in the treatment composition. Alternatively or additionally, the confirming of step (2) can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition.

In another example of the first aspect, the combination of the predetermined temperature and the predetermined rate is sufficient to cause inactivation of the virus in the treatment composition by the virus-inactivation reagent during step (4) by a factor of at least $1\times10^1$. In another example of the first aspect, the predetermined temperature is between 17 and 40° C. and the predetermined rate is 0.3 to 3 times the internal volume of the treatment vessel per hour.

In another example of the first aspect, the internal volume of the treatment vessel is sufficiently large to ensure that not more than one part per million of the treatment composition has a residence time in the treatment vessel of a shorter duration than that required to cause inactivation of the virus in the treatment composition by the virus-inactivation reagent during step (4) by a factor of at least $1\times10^1$.

In another example of the first aspect, steps (1) to (5) are carried out continuously for at least one hour.

In another example of the first aspect, if there is a failure to confirm that the treatment composition exhibits the predetermined property at step (2), then a corresponding portion of the treatment composition is diverted and thus not transferred during step (3).

In another example of the first aspect, if there is a failure to confirm that the treatment composition exhibits the predetermined property at step (2), then a corresponding portion of the treatment composition is diverted and thus not collected during step (5).

In another example of the first aspect, the biological product is a protein of interest. For example, the protein of interest can comprise an antibody, antibody fragment, or antibody derivative. Also for example, the antibody, antibody fragment, or antibody derivative can be selected from the group consisting of an antibody, a monoclonal antibody, a polyclonal antibody, a mammalian antibody, a murine antibody, a primate antibody, a human antibody, a chimeric antibody, a primatized antibody, a humanized antibody, an immunoglobulin light chain, an immunoglobulin heavy chain, an immunoglobulin light chain and an immunoglobulin heavy chain, an antibody fragment, an antibody derivative, an Fab fragment, an F(ab')$_2$ fragment, an Fc fragment, an Fc-Fc fusion protein, an Fv fragment, a single chain Fv fragment, a single domain Fv fragment, a tetravalent single chain Fv fragment, a disulfide-linked Fv fragment, a diabody, a triabody, a tetrabody, a pentabody, a minibody, a miniantibody, an immunoglobulin single variable domain, an immunoglobulin single variable heavy domain, an immunoglobulin single variable light domain, a VHH domain, a humanized VHH domain, a single-domain antibody, a protein comprising an immunoglobulin single variable domain linked together in a modular format with another immunoglobulin single variable domain or a functional domain, a multivalent protein comprising two or more of the same immunoglobulin single variable domain linked together in a modular format, a biparatopic protein comprising two different immunoglobulin single variable domains linked together in a modular format, a bispecific protein comprising two different immunoglobulin single variable domains linked together in a modular format, a bi-functional protein comprising an immunoglobulin single variable domain and a functional domain linked together in a modular format, a domain-deleted antibody, a fusion polypeptide of an antibody fragment with another peptide or polypeptide, an Fc-peptide fusion, an Fc-toxin fusion, and a fusion of an antibody fragment and a scaffold protein.

In another example of the first aspect, a protein of interest is made according to the method for continuously inactivating a virus during manufacture of a biological product. For example, the protein of interest can be as described above.

In a second aspect of the disclosure, an apparatus for continuously inactivating virus during manufacture of a biological product is provided. The apparatus includes an initial-mixing vessel, a pre-treatment detector chamber, a pre-treatment hold reservoir, a drain valve, and a treatment vessel. The treatment vessel includes an inlet, an outlet, and a static mixer. The inlet and the outlet are positioned at opposite ends of a major axis of the treatment vessel. The static mixer is internal to the treatment vessel along the major axis. The initial-mixing vessel, the pre-treatment detector chamber, the pre-treatment hold reservoir, and the treatment vessel each have an internal volume and are fluidically connected in series. The drain valve is either connected to, and positioned between, the pre-treatment hold reservoir and the inlet of the treatment vessel, or connected to the outlet of the treatment vessel. The ratio of the internal volume of the pre-treatment hold reservoir to the internal volume of the treatment vessel is 0.003 to 0.06.

In an example of the second aspect, the internal volume of the pre-treatment hold reservoir is 25 mL to 14 L, and the internal volume of the treatment vessel is 8 L to 250 L.

In another example of the second aspect, the internal volume of the pre-treatment hold reservoir is 0.63 mL to 1.4 L, and the internal volume of the treatment vessel is 200 mL to 25 L.

In a third aspect of the disclosure, a method of use of the apparatus for continuously inactivating virus during manufacture of a biological product is provided. The method includes a step (1) of combining, in the initial-mixing vessel, (a) a composition including a biological product, and (b) a composition including a virus-inactivation reagent, to obtain (c) a treatment composition having a predetermined property for inactivation of a virus. The method also includes a step (2) of confirming, as the treatment composition passes through the pre-treatment detector chamber, that the treatment composition exhibits the predetermined property. The method also includes a step (3) of transferring, via the pre-treatment hold reservoir, the treatment composition to the treatment vessel, the transferring occurring at the inlet. The method also includes a step (4) of incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property. The method also includes a step (5) of collecting the treatment composition from the treatment vessel at the outlet. In accordance with the method, steps (1) to (5) are carried out continuously.

Each example disclosed above with respect to the first aspect also applies with respect to the third aspect. Thus, for example, in an example of the third aspect the predetermined property of the treatment composition includes at least one of (a) a pH between 3.0 to 3.8 or (b) a detergent concentration between 0.05% and 10% (v/v), like for the corresponding example of the first aspect.

In a fourth aspect of the disclosure, a system for continuously inactivating virus during manufacture of a biological product is provided. The system includes a perfusion bioreactor and an apparatus for continuously inactivating virus during manufacture of a biological product.

In accordance with the system, the apparatus includes an initial-mixing vessel, a pre-treatment detector chamber, a pre-treatment hold reservoir, a drain valve, and a treatment vessel. The treatment vessel includes an inlet, an outlet, and a static mixer. The inlet and the outlet are positioned at opposite ends of a major axis of the treatment vessel. The static mixer is internal to the treatment vessel along the major axis. The initial-mixing vessel, the pre-treatment detector chamber, the pre-treatment hold reservoir, and the treatment vessel each have an internal volume and are fluidically connected in series. The drain valve is either connected to, and positioned between, the pre-treatment hold reservoir and the inlet of the treatment vessel, or connected to the outlet of the treatment vessel. The ratio of the internal volume of the pre-treatment hold reservoir to the internal volume of the treatment vessel is 0.003 to 0.06.

Also in accordance with the system, the perfusion bioreactor and the apparatus are connected via the initial-mixing vessel. The perfusion bioreactor has an internal volume that is 5 to 2400 fold greater than the internal volume of the treatment vessel.

In a fifth aspect of the disclosure, a method of use of the system for continuously inactivating virus during manufacture of a biological product is provided. The method includes a step (0) of transferring, from the perfusion bioreactor to the apparatus via the initial mixing vessel, a composition including a biological product. The method includes a step (1) of combining, in the initial-mixing vessel, (a) the composition including the biological product, and (b) a composition including a virus-inactivation reagent, to obtain (c) a treatment composition having a predetermined property for inactivation of a virus. The method also includes a step (2) of confirming, as the treatment composition passes through the pre-treatment detector chamber, that the treatment composition exhibits the predetermined property. The method also includes a step (3) of transferring, via the pre-treatment hold reservoir, the treatment composition to the treatment vessel, the transferring occurring at the inlet. The method also includes a step (4) of incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property. The method also includes a step (5) of collecting the treatment composition from the treatment vessel at the outlet. In accordance with the method, steps (0) to (5) are carried out continuously.

Each example disclosed above with respect to the first aspect also applies with respect to the fifth aspect. Thus, for example, in an example of the fifth aspect the predetermined property of the treatment composition includes at least one of (a) a pH between 3.0 to 3.8 or (b) a detergent concentration between 0.05% and 10% (v/v), like for the corresponding example of the first aspect.

In a sixth aspect, a method for manufacturing a protein of interest is provided. The method includes a step (I) of cultivating a host cell in a culture medium with expression of a protein of interest by the host cell. The method also includes at least one step (II) of continuously inactivating a virus during manufacture of the protein of interest. The method also includes a step (III) of recovering the protein of interest from the culture medium.

In accordance with the sixth aspect, step (II) includes a step (1) of combining (a) a composition including the protein of interest, and (b) a composition including a virus-inactivation reagent, to obtain (c) a treatment composition having a predetermined property for inactivation of a virus. Step (II) also includes a step (2) of confirming that the treatment composition exhibits the predetermined property. Step (II) also includes a step (3) of transferring the treatment composition to a treatment vessel that includes an inlet, outlet, and a static mixer and having an internal volume, the inlet and the outlet being positioned at opposite ends of a major axis of the treatment vessel and the static mixer being internal to the treatment vessel along the major axis, and the transferring occurring at the inlet. Step (II) also includes a step (4) of incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property. Step (II) also includes a step (5) of collecting the treatment composition from the treatment vessel at the outlet. In accordance with the method, steps (1) to (5) are carried out continuously.

Each example disclosed above with respect to the first aspect also applies with respect to the sixth aspect. Thus, for example, in an example of the sixth aspect the predetermined property of the treatment composition includes at least one of (a) a pH between 3.0 to 3.8 or (b) a detergent concentration between 0.05% and 10% (v/v), like for the corresponding example of the first aspect. Also for example, the protein of interest can include an antibody, antibody fragment, or antibody derivative, like for the corresponding example of the first aspect.

BRIEF DESCRIPTION OF THE DRAWINGS

These and other features, aspects, and advantages of the claimed methods, apparatuses, and systems are better understood when the following detailed description is read with reference to the accompanying drawings, in which:

FIG. 2 is a schematic view of an example treatment vessel 210 for use in a method for continuously inactivating a virus during manufacture of a biological product, in which the treatment vessel 210 has a linear shape;

FIG. 3 is a schematic view of an example treatment vessel 210 for use in a method for continuously inactivating a virus during manufacture of a biological product, in which the treatment vessel 210 has a curved shape;

FIG. 4 is a schematic view of an example treatment vessel 210 for use in a method for continuously inactivating a virus during manufacture of a biological product, in which the treatment vessel 210 has a spiral shape;

DETAILED DESCRIPTION OF THE INVENTION

Figure 1:
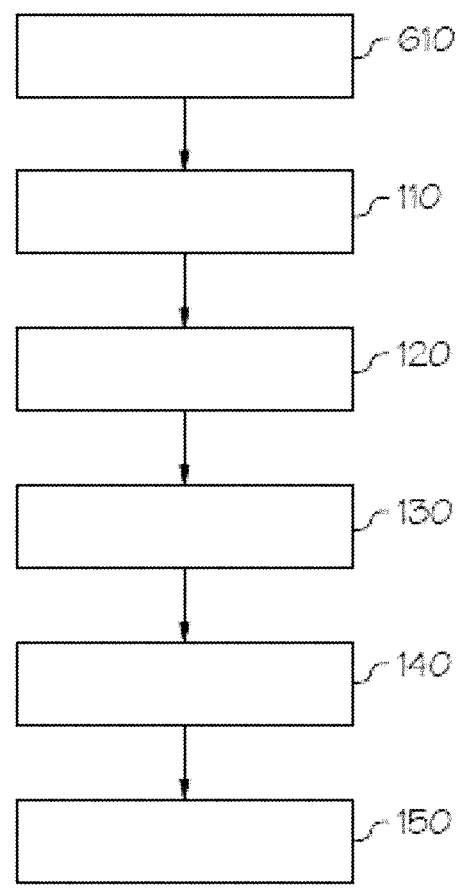
FIG. 1 is a flow chart of a preferred method for continuously inactivating a virus during manufacture of a biological product comprising: a step (1) 110 of combining (a) a composition including a biological product, and (b) a composition including a virus-inactivation reagent, to obtain (c) a treatment composition having a predetermined property for inactivation of a virus; a step (2) 120 of confirming that the treatment composition exhibits the predetermined property; a step (3) 130 of transferring the treatment composition to a treatment vessel that includes an inlet, an outlet, and a static mixer, the transferring occurring at the inlet; a step (4) 140 of incubating the treatment composition in the treatment vessel at a predetermined temperature while the treatment composition flows at a predetermined rate and contacts the static mixer; and a step (5) 150 of collecting the treatment composition from the treatment vessel at the outlet; and optionally a step (O) 610 of transferring, from a perfusion bioreactor to an apparatus for continuously inactivating a virus during manufacture of the biological product via an initial mixing vessel, e.g. directly or indirectly, the composition including the biological product.

Aspects of the claimed methods, apparatuses, and systems will now be described more fully hereinafter with reference to the accompanying drawings in which example embodiments are shown. Whenever possible, the same reference numerals are used throughout the drawings to refer to the same or like parts. However, the claimed methods, apparatuses, and systems may be embodied in many different forms and should not be construed as limited to the embodiments set forth herein. These example embodiments are provided so that this disclosure will be both thorough and complete, and will fully convey the scope of the claimed methods, apparatuses, and systems to those skilled in the art.

In a first aspect of the disclosure, as shown in FIG. 1, a method for continuously inactivating a virus during manufacture of a biological product is provided. As noted above, inactivation of viruses that may be present in a composition including a biological product that is intended for use in a biopharmaceutical product is an important aspect of quality control. The biological product can be, for example, a protein, a nucleic acid, a carbohydrate, a lipid, or a biomaterial, among other substances. The protein can be, for example, a therapeutic protein, such as an antibody, an antibody fragment, an antibody derivative, a cytokine, a growth factor, a hormone, an enzyme, or a blood coagulation factor, among others, or a vaccine protein, such as an antigenic protein, among others. The biological product can be produced by a living system, such as a cell, tissue, or organism, e.g. by a mammalian cell, a plant cell, or a bacterial cell, among others. The biological product can be produced by a homogeneous process, e.g. suspension culture based on use of a stirred-tank bioreactor, air-lift bioreactor, or wave bioreactor, or a heterogeneous process, e.g. adherent culture based on a microcarrier-based system, a packed bed bioreactor, or a hollow-fiber bioreactor, as carried out in a discontinuous mode, e.g. batch cultivation or fed-batch cultivation, or in a continuous mode, e.g. continuous cultivation with perfusion, and as carried out at any suitable scale, e.g. laboratory, pilot, or production scale. The virus may be one that can infect bacteria (i.e. a "bacteriophage," also termed a "phage"), or a human and/or an animal, e.g. the individual human or animal for which the biological product is intended for administration, among others. The virus may have been introduced into the composition including the biological product from an exogenous source, e.g. by inadvertent failure to maintain sterility, or from an endogenous source, e.g. the living system used to make the biological product.

The method can be used to ensure that a virus that may have been present during the manufacture of the biological product, for example based on viral contamination, is inactivated. To the extent that multiple different types of viruses and/or multiple active particles of a given type of virus may be present, the method can be used to inactivate the multiple different types and/or multiple active particles of a given type. Thus, for example, the method can be used to ensure that a biopharmaceutical product that ultimately includes the biological product will not include active particles of virus of any type in any amount above an acceptable limit, e.g. that the biopharmaceutical product will be free of active particles of virus.

As shown in FIG. 1, the method includes a step (1) 110 of combining (a) a composition including a biological product, and (b) a composition including a virus-inactivation reagent, to obtain (c) a treatment composition having a predetermined property for inactivation of a virus.

The predetermined property of the treatment composition for inactivation of a virus can include at least one of a pH between 3.0 to 3.8 or a detergent concentration between 0.05% and 10% (v/v). A pH between 3.0 to 3.8 can cause inactivation of virus, as can a detergent concentration between 0.05% and 10% (v/v). The predetermined property can be predetermined in the sense that an overall process that is sufficient to accomplish inactivation of virus in a treatment composition to a desired extent can be developed, based on preparing a treatment composition having a specific property for inactivation of a virus and testing various conditions to determine and confirm sufficiency, followed by application of the process during manufacture of the biological product generally. Such application can include combining a composition including the biological product and a composition including the virus-inactivation reagent to obtain a treatment composition having the predetermined property for inactivation of a virus, i.e. the method can be carried out in accordance with a specific plan to ensure inactivation of a virus that may be present. Thus, in some examples the predetermined property of the treatment composition includes a pH between 3.0 to 3.8, e.g. 3.3 to 3.8, or 3.5 to 3.8. In some examples the predetermined property of the treatment composition includes a detergent concentration between 0.05% and 10% (v/v), e.g. between 0.05% and 5.0% (v/v), or between 0.05% and 2.0% (v/v). In some examples the predetermined property of the treatment composition includes both a pH between 3.0 to 3.8 and a detergent concentration between 0.05% and 10% (v/v), for example a pH between 3.3 to 3.8 and a detergent concentration between 0.05% and 5.0% (v/v), or a pH between 3.3 to 3.8 and a detergent concentration between 0.05% and 2.0% (v/v), or a pH between 3.5 to 3.8 and a detergent concentration between 0.05% and 5.0% (v/v), or a pH between 3.5 to 3.8 and a detergent concentration between 0.05% and 2.0% (v/v).

The composition including the biological product can be, for example, a composition derived directly from a bioreactor, e.g. a bioreactor being used for production of the biological product by a living system such as a mammalian cell culture. The composition including the biological product can be, for example, one obtained from a bioreactor being operated in a continuous mode, e.g. continuous cultivation with perfusion, and thus can include a cell culture medium, having been utilized to some extent by cells of a mammalian cell culture, and the biological product, as secreted from the cells. The composition including the biological product also can be, for example, a composition derived indirectly from a bioreactor, e.g. following one or more processing steps, such as filtration, precipitation, and/or chromatographic separation, among other steps, to remove some or all unwanted debris, compounds, and other substances prior to subjecting the composition including the biological product to the method for continuously inactivating a virus.

The virus-inactivation reagent can include, for example, at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm.

An acid having a titratable group having a pKa between 2.3 to 4.2 and not having another titratable group having a pKa between 4.2 and 8.5 means an acid that has at least one titratable group that has a pKa between 2.3 and 4.2, and that may have additional titratable groups having a pKa below 2.3 or above 8.5, but that does not have another titratable group that has a pKa between 4.2 and 8.5, each pKa as determined at about 20 to 25° C.

An organic acid, such as for example a carboxylic acid or an amino acid, having a pKa between 2.3 to 4.2 and not having another titratable group having a pKa between 4.2 and 8.5 is such an acid. Such organic acids include, for example, lactic acid, which has a titratable group having a pKa of 3.86 at 25° C., and which does not have another titratable group having a pKa between 4.2 and 8.5. Formic acid, which has a titratable group having a pKa of about 3.74 at 20° C., and which does not have another titratable group having a pKa between 4.2 and 8.5, also is such an organic acid. Ascorbic acid, which has a titratable group having a pKa of 4.17 at about 20 to 25° C. and an additional titratable group that has a pKa of 11.6 also at about 20 to 25° C., and which does not have another titratable group having a pKa between 4.2 and 8.5, also is such an organic acid. Glycine, which has a titratable group having a pKa of 2.34 at about 20 to 25° C., and which does not have another titratable group having a pKa between 4.2 and 8.5, also is such an organic acid. Thus, for example, the virus-inactivation reagent can be an acid having a titratable group having a pKa between 2.3 to 4.2 and not having another titratable group having a pKa between 4.2 and 8.5 selected from the group consisting of an organic acid having a titratable group having a pKa between 2.3 to 4.2 and not having another titratable group having a pKa between 4.2 and 8.5, lactic acid, formic acid, ascorbic acid, an amino acid having a titratable group having a pKa between 2.3 to 4.2 and not having another titratable group having a pKa between 4.2 and 8.5, glycine, or a combination thereof.

The acid having a titratable group having a pKa between 2.3 to 4.2 and not having another titratable group having a pKa between 4.2 and 8.5 can be useful in the method for at least the following reasons. First, by having a titratable group having a pKa between 2.3 to 4.2, the acid can adequately buffer the treatment composition at a pH between 3.0 to 3.8 without need for including high amounts of the acid, e.g. the acid can be present in the treatment composition at or below 100 mM and still provide sufficient buffering capacity. This can ensure maintenance of the treatment composition at a pH between 3.0 to 3.8, the pH being low enough to enable inactivation of virus, but high enough to avoid harm to the biological product, e.g. acid denaturation of protein. Second, by not having another titratable group having a pKa between 4.2 and 8.5, the treatment composition including the acid can later be neutralized without need for titration of another titratable group, and thus without need for addition of extra ions that would not otherwise need to be added in the absence of the other titratable group. This can promote effectiveness of any ion exchange step that may be carried out following inactivation of the virus.

Certain particular acids having a titratable group having a pKa between 2.3 to 4.2 and not having another titratable group having a pKa between 4.2 and 8.5 also can be useful for additional reasons. For example, lactic acid is additionally useful because it is naturally present in cells and thus in processes for production of biological products, it is a substance that is Generally Recognized as Safe (also termed "GRAS") by the FDA, and it is inexpensive.

A non-ionic detergent having a chromophoric group having an absorption peak between 230 nm and 600 nm includes, for example, a polyethylene oxide detergent having an aromatic group, among others, which includes for example Triton-X 100 detergent, among others. Thus, for example, the virus-inactivation reagent can be a non-ionic detergent having a chromophoric group having an absorption peak between 230 nm and 600 nm selected from the group consisting of a polyethylene oxide detergent having an aromatic group, Triton-X 100 detergent, and combinations thereof.

The non-ionic detergent having a chromophoric group having an absorption peak between 230 nm and 600 nm can be useful in the method for at least the following reasons. First, if the non-ionic detergent is present in the treatment composition at a suitable concentration, the uncharged hydrophilic groups of the non-ionic detergent can be used to inactivate virus without harming the biological product. Second, the chromophoric group having an absorption peak between 230 nm and 600 nm of the non-ionic detergent can be used for measuring the detergent concentration within the treatment composition, for example based on ultraviolet absorption by the chromophoric group, which is a concentration-dependent characteristic.

Accordingly, the composition including the virus-inactivation reagent can be a composition that includes at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm, e.g. the composition can include one or more of the acids as recited, one or more of the non-ionic detergents as recited, or combinations thereof.

As noted above, the method includes a step (1) 110 of combining (a) a composition including a biological product, and (b) a composition including a virus-inactivation reagent, to obtain (c) a treatment composition having a predetermined property for inactivation of a virus. As will be appreciated, the effectiveness of the virus-inactivation reagent for inactivating virus that may be present will depend on the concentration of the virus-inactivation reagent in the treatment composition, among other factors. As will also be appreciated, the concentration of the virus-inactivation reagent necessary to inactivate a virus to a given extent can be determined empirically under actual conditions, estimated based on prior experience under analogous conditions, and/or predicted based on theory. As will further be appreciated, this concentration also can be used to ensure that the virus-inactivation reagent is included in the composition including the virus-inactivation reagent at a suitable concentration to ensure, upon taking into account the proportional contribution of the composition including the virus-inactivation reagent to the volume of the treatment composition, that the virus-inactivation reagent will be present in the treatment composition at a concentration effective for inactivation of virus. For example, considering use of a virus-inactivation reagent corresponding to one of the acids recited, e.g. lactic acid, if it is determined that the acid should be included in the treatment composition at about 100 mM, and the treatment composition will be prepared by combining about one volume of the composition including the virus-inactivation reagent per nine volumes of the composition including the biological product, then the composition including the virus-inactivation reagent can be prepared including the acid at a concentration of about 1 M. Also for example, considering use of a virus-inactivation reagent corresponding to one of the non-ionic detergents recited, e.g. Triton-X 100 detergent, if it is determined that the non-ionic detergent should be included in the treatment composition at about 1.0% (v/v), and the treatment composition will be prepared by combining about one volume of the composition including the virus-inactivation reagent per nine volumes of the composition including the biological product, then the composition including the virus-inactivation reagent can be prepared including the non-ionic detergent at a concentration of about 10% (v/v).

For a composition including the virus-inactivation reagent corresponding to one or more of the acids as recited, the composition can further have, for example, a pH of 3.0 to 3.8, e.g. a pH of about 3.0, a pH of about 3.3, or a pH of about 3.5. Use of such a composition having a pH of 3.0 to 3.8, instead of, for example, a composition having a pH below or above this range, can ensure that the treatment composition, resulting from combining the composition including the biological product and the composition including the virus-inactivation reagent, will not have a pH lower than 3.0, which may harm the biological product, and will not have a pH above 3.8, which may result in little or no inactivation of virus.

As noted, in accordance with step (1) 110, the composition including the biological product and the composition including the virus-inactivation reagent are combined to obtain a treatment composition having a predetermined property for inactivation of a virus. The combining can be carried out, for example, within a vessel including one or more mixers, such that the composition including the biological product and the composition including the virus-inactivation reagent are added to the vessel, e.g. separately and simultaneously, flow through the vessel, e.g. under pressure, and are mixed while flowing, by the one or more mixers. The mixing can occur, for example, for a period of time, e.g. 1 to 5 minutes, that is sufficiently long to ensure that the treatment composition is mixed to homogeneity, but not so long as for inactivation of the virus to proceed to a substantial extent. Other approaches can also be used.

As also shown in FIG. 1, the method also includes a step (2) 120 of confirming that the treatment composition exhibits the predetermined property. The confirming can be carried out by use of a detector, e.g. a pH meter, a conductivity meter, a temperature meter, a spectrophotometric device, or a spectroscopic device, that can be used to measure a characteristic of the treatment composition, e.g. pH, conductivity, temperature, a spectrophotometric characteristic, or a spectroscopic characteristic.

In this regard, the confirming can be carried out by measuring the predetermined property directly. For example, for the predetermined property corresponding to a pH between 3.0 to 3.8, the confirming can be carried out by measuring the pH of the treatment composition following mixing thereof. This can be accomplished, for example, by use of a pH meter. Also for example, for the predetermined property corresponding to a detergent concentration between 0.05% and 10% (v/v), the confirming can be carried out by measuring the detergent concentration, for example by measuring ultraviolet absorption due to the chromophoric group of the detergent, for example, by use of a spectrophotometric device.

The confirming also can be carried out by measuring the predetermined property indirectly. This can be done, for example, to the extent that another compound has been included in the composition including the virus-inactivation reagent at a known concentration, for which the concentration thereof can be measured, e.g. based on including a salt and measuring its concentration, for example, by use of a conductivity meter.

This can also be done, for example, to the extent that the composition including the biological product and the composition including the virus-inactivation reagent have different temperatures when combined, such that the resulting treatment composition has an initial temperature, following mixing but preceding treatment, that is intermediate therebetween and that is indicative of the relative proportions of the composition including the biological product and the composition including the virus-inactivation reagent in the treatment composition, e.g. based on measuring the initial temperature of the treatment composition, for example, by use of a temperature meter. For example, if Ttc=temperature of the treatment composition, Tbp=temperature of the composition including the biological product, and Tvir=temperature of the composition including the virus-inactivation reagent, then the fraction of composition including the virus-inactivation reagent in the treatment composition can be calculated as (Ttc−Tbp)/(Tvir−Tbp).

This can also be done, for example, to the extent that a compound including a pH-sensitive group is included in the composition including the biological product as provided, for which a spectroscopic characteristic thereof can be measured, for example, by use of a spectroscopic device. Such compounds including a pH-sensitive group can be, for example, the biological product and/or a buffer that is included in the composition including the biological product, and/or can be a chromophoric compound. In accordance with such examples, the spectroscopic characteristic of the pH-sensitive group can be used to confirm the predetermined property indirectly. Also in accordance with such examples, because the compound including the pH-sensitive group is included in the composition including the biological product as provided, the compound may be considered an intrinsic compound with respect to the composition including the biological product, e.g. an intrinsic chromophoric compound.

This can also be done, for example, to the extent that a compound including a pH-sensitive group, that is not included in the composition including the biological product as provided, is subsequently added to the composition including the biological product, is included in the composition including the virus-inactivation reagent, and/or is otherwise added to the treatment composition, again for which a spectroscopic characteristic thereof can be measured, for example, by use of a spectroscopic device. Such compounds including a pH-sensitive group can be, for example, a chemical listed as an FDA-approved GRAS substance that includes a pH-sensitive group and/or an FDA-approved inactive ingredient that includes a pH-sensitive group, and/or can be a chromophoric compound. Again, in accordance with such examples, the spectroscopic characteristic of the pH-sensitive group can be used to confirm the predetermined property indirectly. Also in accordance with such examples, because the compound including the pH-sensitive group is not included in the composition including the biological product as provided, the compound may be considered an extrinsic compound with respect to the composition including the biological product, e.g. an extrinsic chromophoric compound.

For example, the virus-inactivation reagent can be an organic acid having a titratable group having a pKa between 2.3 to 4.2 and not having another titratable group having a pKa between 4.2 and 8.5, lactic acid, formic acid, ascorbic acid, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. For example, if the composition including the biological product has a conductivity of about 10 mS/cm, as would be typical of a product feed obtained directly from a bioreactor being used for continuous cultivation with perfusion, then sodium chloride can be included as the salt in the composition including the virus-inactivation reagent at a concentration of 1 M or higher, and the treatment composition can be prepared by combining about one volume of the composition including the virus-inactivation reagent per nine volumes of the composition including the biological product. This approach would result in an increase of the conductivity of the treatment composition by the salt by about 10% or more, i.e. to about 11 mS/cm or more, which is above the threshold for detection, thus allowing confirmation that salt has been added to the treatment composition in the amount expected, and thus by extrapolation that the virus-inactivation reagent also has been added to the treatment composition in the amount expected. Also for example, if the composition including the biological product has a lower conductivity than 10 mS/cm, e.g. about 2 mS/cm, which can be typical of a product feed following one or more processing steps, then the sodium chloride can be included in the composition including the virus-inactivation reagent at a proportionally lower concentration, and following combination still increase the conductivity of the treatment composition by about 10% or more, again above the threshold for detection. Salts other than sodium chloride can also be used, upon taking into account any differences in conductivities between the salts.

Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. For example, the composition including the biological product may have a temperature that is lower (or, alternatively higher) than the temperature of the composition including the virus-inactivation reagent, upon mixing, such that the resulting treatment composition has an initial temperature intermediate therebetween. In accordance with this example, the initial temperature of the treatment composition is indicative of the relative proportions of the composition including the biological product and the composition including the virus-inactivation reagent in the treatment composition. This in turn can be used to determine the concentration of the virus-inactivation reagent in the treatment composition.

Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. For example, a chromophoric compound having a titratable group having a pKa of about 2.5 to 5.0, such as various carboxylic acid compounds and sulphonate compounds, can be used. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. For example, the biological product itself may include a pH-sensitive group that exhibits a pH-sensitive change in fluorescence spectrum that can be used to measure pH of the treatment composition. Also for example, a buffer included in the composition including the biological product may include a pH-sensitive group that exhibits a pH-sensitive change in fluorescence spectrum that can be used to measure pH of the treatment composition. Also for example, one or more other compounds present in the composition including the biological product may include a pH-sensitive group that exhibits a pH-sensitive change in ultra-violet spectrum, visible spectrum, infra-red spectrum, and/or Raman spectrum that can be used to measure pH of the treatment composition. Accordingly, the corresponding compound including the pH-sensitive group can be, for example, an intrinsic chromophoric compound. The use of such a pH-sensitive group, e.g. a pH-sensitive group of an intrinsic chromophoric compound, can be advantageous because the pH of the composition including the biological product and/or the treatment composition can be measured spectrally without need for adding any extraneous compounds thereto.

Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition. For example, the compound including a pH-sensitive group can be, for example, a chemical listed as an FDA-approved GRAS substance and/or an FDA-approved inactive ingredient, and/or an extrinsic chromophoric compound. The use of such a pH-sensitive group, e.g. a pH-sensitive group of an extrinsic chromophoric compound, can be advantageous because the pH-sensitive group can be added to the composition including the biological product and the composition including the virus-inactivation reagent at concentrations chosen to ensure that the treatment composition is prepared including the pH-sensitive group at a constant concentration, thus limiting variability of the spectroscopic characteristic of the treatment composition that might otherwise occur due to variation in the concentration of the pH sensitive group. Moreover, the use of a corresponding extrinsic chromophoric compound that is an FDA-approved GRAS substance and/or an FDA-approved inactive ingredient also can be advantageous based on minimizing risk to patients to whom a final drug product including the biological product is administered, because even if the final drug product may contain trace amounts of the extrinsic chromophoric compound, the final drug product still will be safe for patients.

Also for example, the virus-inactivation reagent can be an amino acid having a titratable group having a pKa between 2.3 to 4.2 and not having another titratable group having a pKa between 4.2 and 8.5, glycine, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be a polyethylene oxide detergent having an aromatic group, Triton-X 100 detergent, or a combination thereof, and the predetermined property of the treatment composition can include a detergent concentration between 0.05% and 10% (v/v). In accordance with this example, the confirming of step (2) 120 can include measuring ultraviolet absorption of the treatment composition, wherein the ultraviolet absorption indicates the concentration of the detergent in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. This in turn can be used to determine the detergent concentration of the treatment composition.

As noted above, the confirming can be carried out by use of a detector, e.g. a pH meter, a conductivity meter, a temperature meter, a spectrophotometric device, or a spectroscopic device, that can be used to measure a characteristic of the treatment composition. For example, the confirming can be carried out as the composition flows through a detector chamber, e.g. a chamber in which a pH probe of the pH meter, a conductivity probe of the conductivity meter, or a temperature probe of the temperature meter, is in contact with the treatment composition, or a chamber in which the treatment composition can be subjected to spectrophotometric or spectroscopic analysis of the spectrophotometric or spectroscopic device. The treatment composition can reach the detector chamber, for example, based on flowing under pressure from a vessel in which the treatment composition was prepared, as described above, to the detector chamber, with the two being fluidically connected, i.e. connected such that a fluid can flow internally and at least unidirectionally from the vessel in which the treatment composition was prepared to the detector chamber.

As also shown in FIG. 1, with reference to FIG. 2, the method also includes a step (3) 130 of transferring the treatment composition to a treatment vessel 210 that includes an inlet 220, an outlet 230, and a static mixer 240 and having an internal volume 212, the inlet 220 and the outlet 230 being positioned at opposite ends, i.e. an inlet end 250 and an outlet end 260, of a major axis 270 of the treatment vessel 210 and the static mixer 240 being internal to the treatment vessel 210 along the major axis 270, and the transferring occurring at the inlet 220. As shown in FIG. 2, the treatment vessel 210 can be in the form of, for example, a column or a tube, among other forms. As shown in FIG. 2, FIG. 3, and FIG. 4, respectively, the treatment vessel 210 can have a shape that is, for example, linear, curved, or spiral, among other shapes, and thus can have a major axis 270 that also is, for example, linear, curved, or spiral, among other types. The treatment vessel 210 can be made from, for example, a metal, a plastic, or a combination thereof, among other materials. The treatment vessel can include one static mixer 240, or multiple static mixers 240, e.g. two, three, four, or more, as appropriate to ensure effective mixing, as discussed below. The static mixer can be a type of static mixer that includes, for example, baffles, orifices, impingement plates, and/or other in-line protuberances. The static mixer can be made of one or more materials that are compatible with biopharmaceutical processing, e.g. one or more of metal, plastic, rubber, and/or glass compatible with biopharmaceutical processing.

The transferring of the treatment composition to the treatment vessel 210 at the inlet 220 can occur, for example, based on the treatment composition flowing under pressure from a detector chamber, as described above, to the treatment vessel 210, with the detector chamber and the treatment vessel 210 being fluidically connected, i.e. connected such that a fluid can flow internally and at least unidirectionally from the detector chamber to the treatment vessel 210. The rate of the transferring can be controlled, e.g. by a pump, with the treatment composition passing through a reservoir, fluidically connected to the detector chamber and the treatment vessel 210, and positioned therebetween, to ensure that any particular portion of the treatment composition that is not confirmed to exhibit the predetermined property during step (2) 120 can be diverted away from the treatment vessel 210, rather than reaching the treatment vessel 210.

As also shown in FIG. 1, with reference to FIG. 2, the method also includes a step (4) 140 of incubating the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property. Accordingly, to the extent that a virus is present in the treatment composition prior to step (4) 140, e.g. as multiple different types of viruses and/or multiple active particles of a given type of virus, the virus will be inactivated to at least some extent based on incubation in the treatment vessel 210 during step (4) 140.

The treatment vessel 210 can be maintained at the predetermined temperature, for example, by use of a heating element, and the flow of the treatment composition can be maintained at the predetermined rate, for example, by use of a pump.

The predetermined temperature and the predetermined rate can be predetermined in the sense that an overall process rate sufficient to accomplish inactivation of virus to a desired extent can be developed, based on incubating the treatment composition in the treatment vessel 210 at a specific temperature and for a specific time and testing various conditions to determine and confirm sufficiency, followed by application of the process during manufacture of the biological product generally, including controlling the temperature of the treatment vessel 210 and controlling the rate of flow of the treatment composition through the treatment vessel 210 in order to ensure that the treatment composition is subjected to a treatment sufficient to accomplish inactivation of the virus to a desired extent. Again, the method can be carried out in accordance with a specific plan to ensure inactivation of virus that may be present.

The combination of the predetermined temperature and the predetermined rate can be sufficient to cause inactivation of the virus in the treatment composition by the virus-inactivation reagent during step (4) 140 by a factor of at least $1 \times 10^1$. For example, the combination of the predetermined temperature and the predetermined rate can be sufficient to cause inactivation of the virus in the treatment composition by the virus-inactivation reagent during step (4) 140 by a factor of at least $1 \times 10^2$, at least $1 \times 10^3$, at least $1 \times 10^4$, at least $1 \times 10^5$, or at least $1 \times 10^6$. In accordance with this example, the combination of the predetermined temperature and the predetermined rate can be sufficient to cause inactivation of the virus in the treatment composition by the virus-inactivation reagent to at least the extent indicated under a condition of actual viral contamination, as well as under a condition for which viral contamination may be present, whether or not viral contamination is actually present. Moreover, the sufficiency of the combination of the predetermined temperature and the predetermined rate to cause inactivation of the virus can relate to inactivation with respect to a specific type of virus, multiple specific types of viruses, and/or a general or diverse range of viruses. In addition, the sufficiency of the combination of the predetermined temperature and the predetermined rate to cause inactivation of the virus can relate to inactivation with respect to only a portion of the treatment composition subjected to incubation during step (4) 140, e.g. to a portion of the treatment composition incubated in the treatment vessel 210 during a part of the period that the method is being carried out, or to all of the treatment composition subjected to incubation during step (4) 140, e.g. all of the treatment composition so incubated during the entire period that the method is carried out, from start to finish.

The predetermined temperature can be between 17 and 40° C. and the predetermined rate can be 0.3 to 3 times the internal volume 212 of the treatment vessel 210 per hour. In general, as the predetermined temperature is increased, the predetermined rate can also be increased, and vice versa. Conversely, as the predetermined temperature is decreased, the predetermined rate may need to be decreased, and vice versa. This is because the virus-inactivation reagent typically can inactivate virus in the treatment composition more rapidly at a higher temperature, and thus the treatment composition can be incubated in the treatment vessel 210 for a shorter time while still accomplishing inactivation of the virus to a desired extent. For example, the predetermined temperature can be between 18 and 25° C. and the predetermined rate can be 0.5 to 1.5 times the internal volume 212 of the treatment vessel 210 per hour. Also for example, the predetermined temperature can be between 30 and 39° C. and the predetermined rate can be 0.8 to 2.0 times the internal volume 212 of the treatment vessel 210 per hour.

The internal volume 212 of the treatment vessel 210 can be sufficiently large to ensure that not more than one part per million of the treatment composition has a residence time in the treatment vessel 210 of a shorter duration than that required to cause inactivation of the virus in the treatment composition by the virus-inactivation reagent during step (4) 140 by a factor of at least $1 \times 10^1$. In this regard, the treatment vessel 210 can be made or selected based on having an internal volume 212 that is sufficiently large to account for axial dispersion of the treatment composition as the treatment composition flows through the treatment vessel 210, i.e. dispersion of the treatment composition along the major axis of the treatment vessel 210, to control and minimize proportions of the treatment composition that can flow through treatment vessel in less time than would be required to cause inactivation of the virus in the treatment composition by the virus-inactivation reagent during step (4) 140 by a factor of at least $1 \times 10^1$. For example, the treatment vessel 210 can be made or selected based on having an internal volume 212 that includes an extra volume beyond a theoretical plug flow volume in order to account for axial dispersion. The theoretical plug flow volume Vh* of a vessel can be calculated as the product of the critical hold time Tr and the volumetric flow rate Q of a composition within the vessel. The extra volume necessary to account for axial dispersion can be estimated, for example, by using the Taylor dispersion model for laminar flow, or a plug flow, a Gaussian model for turbulent flow, or a model developed specifically for a given static mixer 240, among other approaches. Thus, for example, the internal volume 212 of the treatment vessel 210 can be sufficiently large to ensure that not more than one part per million of the treatment composition, e.g. not more than one part per ten million, one part per hundred million, or one part per billion, has a residence time in the treatment vessel 210 of a shorter duration than that required to cause inactivation of the virus in the treatment composition by the virus-inactivation reagent during step (4) 140 by a factor of at least $1 \times 10^1$, e.g. by a factor of at least $1 \times 10^2$, at least $1 \times 10^3$, at least $1 \times 10^4$, at least $1 \times 10^5$, or at least $1 \times 10^6$. Also for example, the internal volume 212 of the treatment vessel 210 can be sufficiently large to ensure that not more than one part per million of active particles of virus in the treatment composition, e.g. not more than one part per ten million, one part per hundred million, or one part per billion, has a residence time in the treatment vessel 210 of a shorter duration than that required to cause inactivation of the virus in the treatment composition by the virus-inactivation reagent during step (4) 140 by a factor of at least $1 \times 10^1$, e.g. by a factor of at least $1 \times 10^2$, at least $1 \times 10^3$, at least $1 \times 10^4$, at least $1 \times 10^5$, or at least $1 \times 10^6$.

As noted, the treatment composition contacts the static mixer 240 as the treatment composition flows along the major axis 270 of the treatment vessel 210, e.g. including contacting multiple static mixers 240 for treatment vessels 210 that include multiple static mixers 240. This contacting provides for continuous mixing of the treatment composition as the treatment composition flows through the treatment vessel 210, thus minimizing axial dispersion of the treatment composition.

As also shown in FIG. 1, the method also includes a step (5) 150 of collecting the treatment composition from the treatment vessel 210 at the outlet 230. The collecting can correspond to, for example, allowing the treatment composition to continue to flow to another vessel, e.g. for neutralization or removal of the virus-inactivation reagent, for further processing, such as chromatographic separation, or for further inactivation of virus, e.g. by first carrying out inactivation of virus by use of an organic acid as recited above, then carrying out inactivation of virus by use of a detergent as recited above, or by first carrying out inactivation of virus by use of an amino acid as recited above, then carrying out inactivation of virus by use of a detergent as recited above, among other things. The collecting also can correspond to allowing the treatment composition to flow into a container for storage, e.g. for later processing, among other things.

In accordance with the method, step (1) 110, step (2) 120, step (3) 130, step (4) 140, and step (5) 150 are carried out continuously, i.e. each step is carried out simultaneously, on different portions of the composition including the biological product, the composition including the virus-inactivation reagent, and the treatment composition, for at least some period of time. For example, step (1) 110, step (2) 120, step (3) 130, step (4) 140, and step (5) 150 can be carried out continuously for at least one hour, for at least 4 hours, for at least 12 hours, for at least 24 hours, for at least 3 days, for at least 10 days, or for at least 30 days, among other amounts of time. Also for example, step (1) 110, step (2) 120, step (3) 130, step (4) 140, and step (5) 150 can be carried out continuously, not just during overall manufacturing of the biological product, but simultaneous to, and continuous with, actual production of the biological product by a living system during manufacture of the biological product.

In accordance with the method, if there is a failure to confirm that the treatment composition exhibits the predetermined property at step (2) 120, then a corresponding portion of the treatment composition can be diverted, such that it will not be processed to completion. In this regard, under some circumstances as the method is being carried out it may be determined that a portion of a treatment composition does not exhibit the predetermined property for inactivation of virus, due for example to a variation or defect associated with the composition including the biological product, the composition including the virus-inactivation reagent, and/or the proportions at which the two have been combined and mixed to obtain the treatment composition, among other variables and defects. Under such circumstances, the corresponding portion of the treatment composition may be considered or determined to be out of specification, such that virus inactivation may not occur to the extent intended. Moreover, under such circumstances it may be preferable to divert the corresponding portion of the treatment composition rather than to complete processing thereof, e.g. to avoid an undue risk that a pharmaceutical product ultimately prepared from the treatment composition may be contaminated with virus. Once the corresponding portion of the treatment composition has been diverted, the method can be resumed with respect to carrying out step (1) 110, step (2) 120, step (3) 130, step (4) 140, and step (5) 150 continuously, and this cycle can be repeated as often as needed, e.g. once, twice, three times, or more, e.g. over the course of at least 24 hours, at least 3 days, at least 10 days, or at least 30 days, and/or until completion of production the biological product.

Thus, for example, if there is a failure to confirm that the treatment composition exhibits the predetermined property at step (2) 120, then a corresponding portion of the treatment composition can be diverted and thus not transferred during step (3) 130. The corresponding portion of the treatment composition can include some, most, or all of the portion of the treatment composition that did not exhibit the predetermined property at step (2) 120. Moreover, the corresponding portion of the treatment composition can further include portions of the treatment composition that did exhibit the predetermined property at step (2) 120, e.g. some portions of the treatment composition preceding and following the portion of the treatment composition that did not exhibit the predetermined property at step (2) 120. In this way, the method can be used to ensure that any particular portion of the treatment composition that is not confirmed to exhibit the predetermined property during step (2) 120 can be discarded rather than ultimately being included in a biopharmaceutical product that will include the biological product. For example, as noted above, the rate of the transferring of step (3) 130 can be controlled, e.g. by a pump, with the treatment composition passing through a reservoir, fluidically connected to the detector chamber and the treatment vessel 210, and positioned therebetween, to ensure that any particular portion of the treatment composition that is not confirmed to exhibit the predetermined property during step (2) 120 can be diverted away from the treatment vessel 210, rather than reaching the treatment vessel 210.

Also for example, if there is a failure to confirm that the treatment composition exhibits the predetermined property at step (2) 120, then a corresponding portion of the treatment composition can be diverted and thus not collected during step (5) 150. In this way too, the method can be used to ensure that any particular portion of the treatment composition that is not confirmed to exhibit the predetermined property during step (2) 120 can be discarded rather than ultimately being included in a biopharmaceutical product that will include the biological product. For example, the rate of the transferring of step (3) 130 and the predetermined rate of flow of step (4) 140 can be controlled, e.g. again by a pump, with the treatment composition passing through a reservoir, as described, then through the treatment vessel 210, to ensure that any particular portion of the treatment composition that is not confirmed to exhibit the predetermined property during step (2) 120 can be diverted away from further processing downstream of step (4) 140, e.g. following emergence of the portion of the treatment composition from the outlet 230 of the treatment vessel 210, rather than collecting the treatment composition from the treatment vessel 210 at the outlet 230 during step (5) 150.

Figure 5:
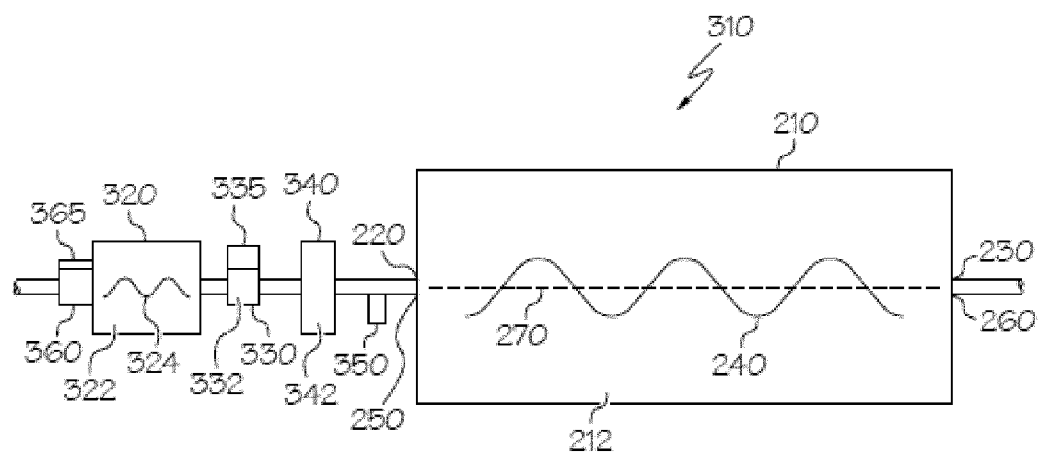
FIG. 5 is a schematic view of an example apparatus 310 for continuously inactivating a virus during manufacture of a biological product, including the treatment vessel 210 of FIG. 2, in which a drain valve 350 is connected to, and positioned between, a pre-treatment hold reservoir 340 and an inlet 220 of the treatment vessel 210.
Figure 6:
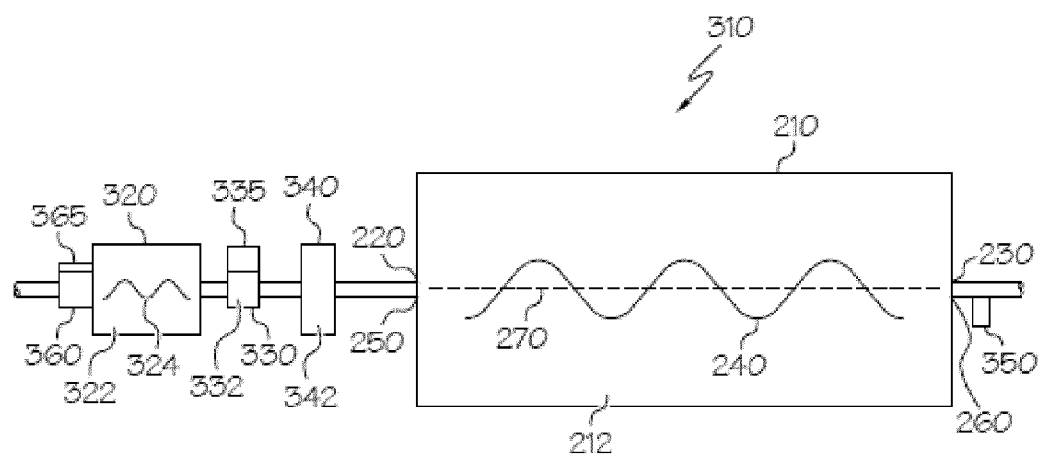
FIG. 6 is a schematic view of an example apparatus 310 for continuously inactivating a virus during manufacture of a biological product, including the treatment vessel 210 of FIG. 2, in which a drain valve 350 is connected to an outlet 230 of the treatment vessel 210.

In a second aspect of the disclosure, as shown in FIG. 5, an apparatus 310 for continuously inactivating a virus during manufacture of a biological product is provided. The apparatus 310 includes an initial-mixing vessel 320, a pre-treatment detector chamber 330, a pre-treatment hold reservoir 340, a drain valve 350, and a treatment vessel 210. The treatment vessel 210 includes an inlet 220, an outlet 230, and a static mixer 240. The inlet 220 and the outlet 230 are positioned at opposite ends, i.e. an inlet end 250 and an outlet end 260, of a major axis 270 of the treatment vessel 210. The static mixer 240 is internal to the treatment vessel 210 along the major axis 270. The initial-mixing vessel 320, the pre-treatment detector chamber 330, the pre-treatment hold reservoir 340, and the treatment vessel 210 each have an internal volume, i.e. internal volumes 322, 332, 342, and 212, respectively, and are fluidically connected in series, e.g. directly or indirectly, such that a fluid can flow internally and at least unidirectionally from the initial-mixing vessel 320, to the pre-treatment detector chamber 330, then to the pre-treatment hold reservoir 340, and then to the treatment vessel 210. As shown in FIG. 5 and FIG. 6, respectively, the drain valve 350 is either connected to, and positioned between, the pre-treatment hold reservoir 340 and the inlet 220 of the treatment vessel 210, or connected to the outlet 230 of the treatment vessel 210. The ratio of the internal volume 342 of the pre-treatment hold reservoir 340 to the internal volume 212 of the treatment vessel 210 is 0.003 to 0.06.

Considering the apparatus 310 in more detail, as shown in FIG. 5, the initial-mixing vessel 320 can be a vessel suitable for combining (a) a composition including a biological product, and (b) a composition including a virus-inactivation reagent, to obtain (c) a treatment composition having a predetermined property for inactivation of a virus, as discussed above. The initial-mixing vessel 320 can include one or more initial mixers 324, such that following addition of the composition including the biological product and the composition including the virus-inactivation reagent to the initial-mixing vessel 320, e.g. separately but simultaneously, and flow thereof through the initial-mixing vessel 320, e.g. under pressure, the compositions can contact the one or more initial mixers 324, resulting in the compositions being mixed together and thus combined.

The pre-treatment detector chamber 330 can be, for example, a chamber in which a pH probe, conductivity probe, or temperature probe is in contact with the treatment composition, or a chamber in which the treatment composition can be subjected to spectrophotometric or spectroscopic analysis. The treatment composition can reach the pre-treatment detector chamber 330, for example, based on flowing under pressure from the initial-mixing vessel 320 in which the treatment composition was prepared, as described above, to the pre-treatment detector chamber 330, based on the two being fluidically connected in series, e.g. directly or indirectly, as noted.

The pre-treatment hold reservoir 340 can be a reservoir, e.g. a tank or a tube, suitable for allowing transfer of the treatment composition to the treatment vessel 210 at the inlet 220 to occur, for example, based on the treatment composition flowing under pressure from the pre-treatment detector chamber 330, as described above, to the treatment vessel 210, with pre-treatment hold reservoir 340 being fluidically connected to the pre-treatment detector chamber 330 and the treatment vessel 210, e.g. directly or indirectly, and positioned therebetween, as noted. The apparatus 310 can be configured, for example, to allow the rate of the transfer to be controlled, e.g. by a pump, to ensure that any particular portion of the treatment composition that is not confirmed to exhibit the predetermined property during passage through the pretreatment detector chamber 320 can be diverted away from the treatment vessel 210, rather than reaching the treatment vessel 210, or can be diverted after flowing through the treatment vessel 210, rather than being collected.

The treatment vessel 210 can be as described above. Accordingly, as shown in FIG. 2, the treatment vessel 210 can be in the form of, for example, a column or a tube, among other forms, as shown in FIG. 2, FIG. 3, and FIG. 4, respectively, the treatment vessel 210 can have a shape that is, for example, linear, curved, or spiral, among other shapes, and thus can have a major axis 270 that also is, for example, linear, curved, or spiral, among other types, and the treatment vessel 210 can be made from, for example, a metal, a plastic, or a combination thereof, among other materials. Moreover, as shown in FIG. 5, the treatment vessel 210 can be used to incubate the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property. Additionally, the treatment composition can be collected from the treatment vessel 210 at the outlet 230.

As noted above, as shown in FIG. 5 and FIG. 6, respectively, the drain valve 350 is either connected to, and positioned between, the pre-treatment hold reservoir 340 and the inlet 220 of the treatment vessel 210, or connected to the outlet 230 of the treatment vessel 210. The drain valve 350 can be used to divert the treatment composition, e.g. if there is a failure to confirm that the treatment composition exhibits a predetermined property, as discussed above.

As also noted above, the ratio of the internal volume 342 of the pre-treatment hold reservoir 340 to the internal volume 212 of the treatment vessel 210 is 0.003 to 0.06. In accordance with this ratio, when the treatment vessel 210 is used to cause inactivation of the virus in the treatment composition, such that the predetermined temperature is between 17 and 40° C. and the predetermined rate is 0.3 to 3 times the internal volume 212 of the treatment vessel 210 per hour, then the residence time of the treatment composition in the pre-treatment hold reservoir 340 will be about 1 to 5 minutes.

Figure 7:
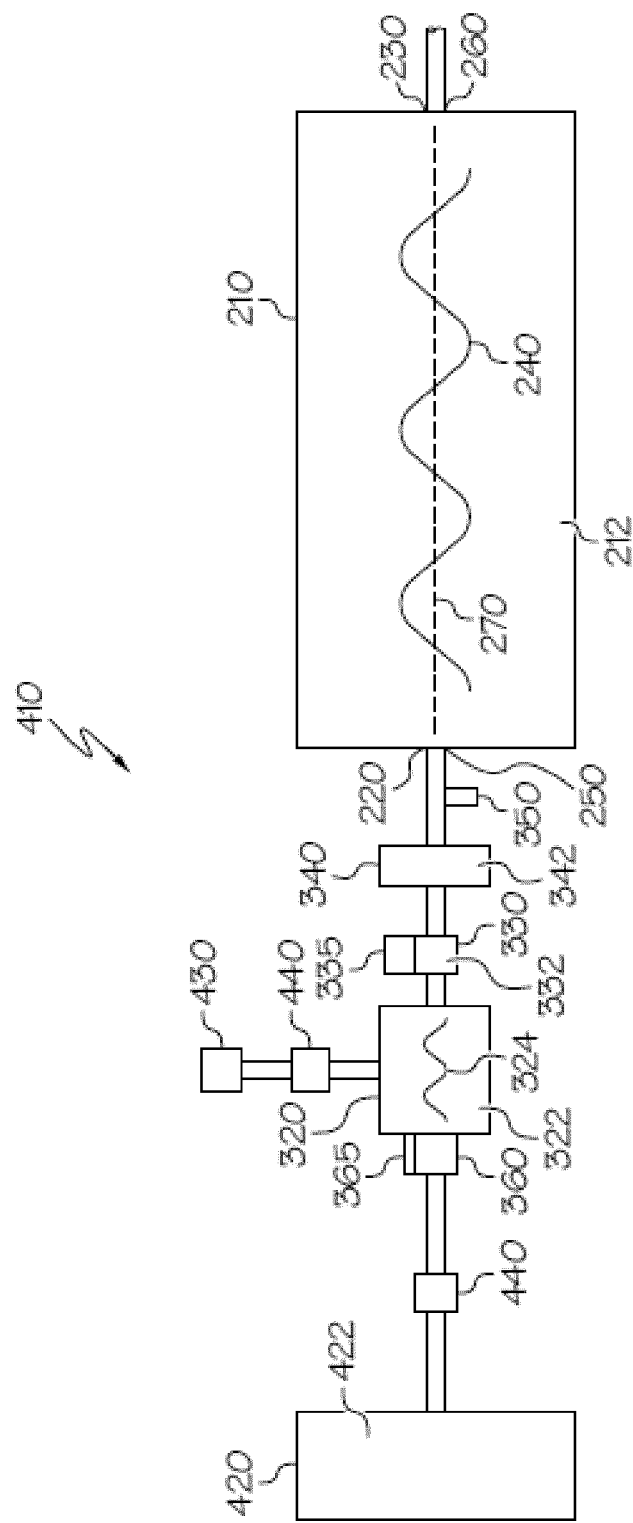
FIG. 7 is a schematic view of an example system 410 for continuously inactivating a virus during manufacture of a biological product, including a perfusion bioreactor 420 and the apparatus 310 of FIG. 5.
Figure 8:
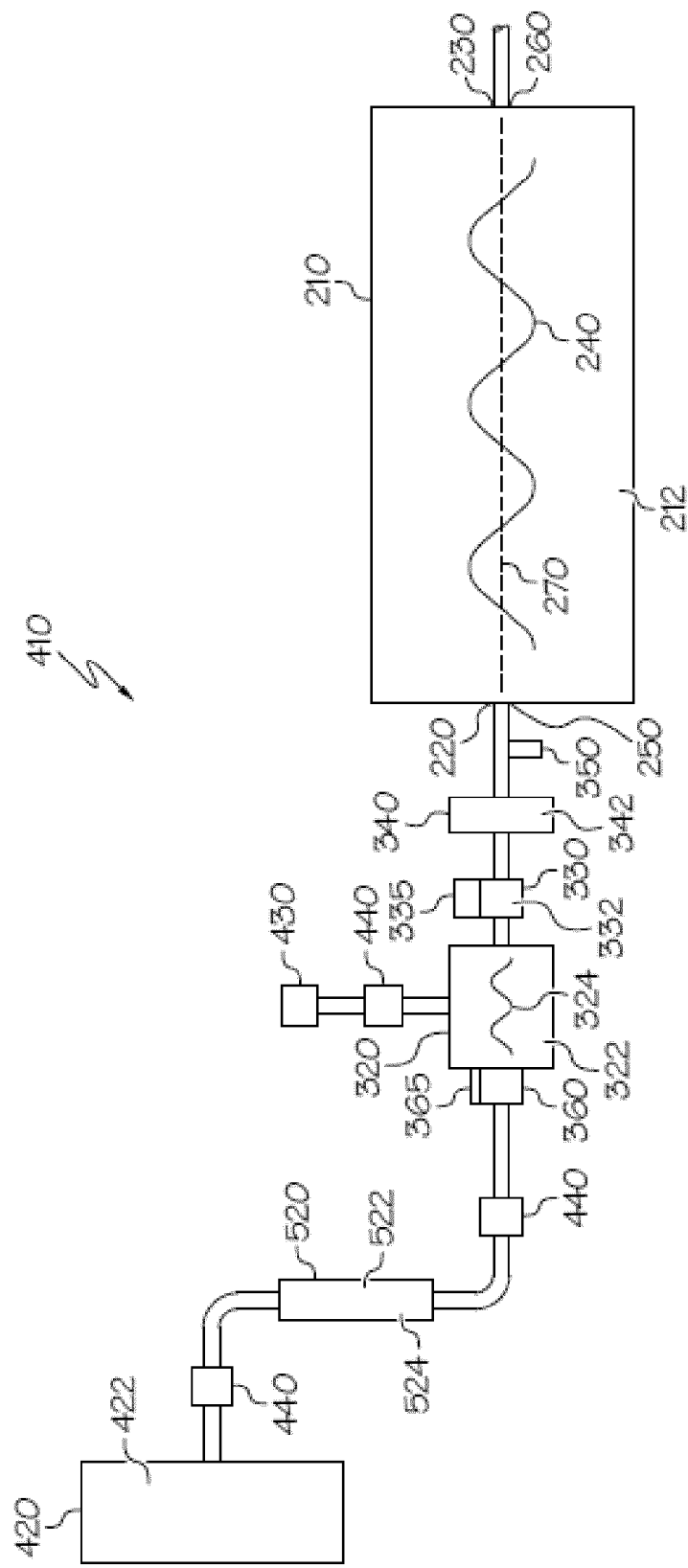
FIG. 8 is a schematic view of an example system 410 for continuously inactivating a virus during manufacture of a biological product, including a perfusion bioreactor 420, a chromatography column 520, and the apparatus 310 of FIG. 5.

As shown in FIG. 7 and FIG. 8, with reference to FIG. 5, the apparatus 310 can be configured for continuously inactivating virus during manufacture of a biological product, for example based on connection to a perfusion bioreactor 420, e.g. a bioreactor configured for use, with a cell separation device, in continuous cultivation with perfusion. The perfusion bioreactor 420 can have a working volume 422, i.e. a volume that can be usefully occupied by a cell culture during operation of the perfusion bioreactor 420 during manufacture of the biological product, corresponding to an internal volume of the perfusion bioreactor 420 minus a head space of the perfusion bioreactor 420. The working volume 422 can be determined based on the design of the perfusion bioreactor 420. In some examples, the working volume 422 can be about 60% to 100%, about 70% to 90%, about 75% to 85%, or about 80% of the internal volume of the perfusion bioreactor 420.

For example, as shown in FIG. 7, the apparatus 310 can be connected to a perfusion bioreactor 420 via the initial-mixing vessel 320, e.g. directly or indirectly, during operation of the perfusion bioreactor 420, such that a composition including a biological product flows from the perfusion bioreactor 420 to the initial-mixing vessel 320 without first being subjected to a processing step, such as filtration, precipitation, and/or chromatographic separation.

Also for example, as shown in FIG. 8, the apparatus 310 can be connected to a perfusion bioreactor 420 via the initial-mixing vessel 320, indirectly, during operation thereof, such that a composition including a biological product flows from the perfusion bioreactor 420 to at least one processing device, e.g. a chromatography column 520 having an internal volume 522 and including a chromatography matrix 524, is subjected to a processing step, such as filtration, precipitation, and/or chromatographic separation, and then flows to the initial-mixing vessel 320. In some examples there is one processing device, e.g. one chromatography column 520, between the perfusion bioreactor 420 and the initial-mixing vessel 320. Also, in some examples there are two, three, four, or more processing devices, e.g. two, three, four, or more chromatography columns 520, between the perfusion bioreactor 420 and the initial-mixing vessel 320. The chromatography matrix 524 can be, for example, a protein A antibody affinity chromatography matrix or an anion exchange chromatography matrix, among other suitable matrices.

The pre-treatment hold reservoir 340 and the treatment vessel 210 can be made or selected such that the respective internal volumes 342 and 212 thereof are dimensioned proportionally to a perfusion bioreactor 420 to which the apparatus 310 is connected and a perfusion rate at which the perfusion bioreactor 420 is being operated. Such dimensioning can facilitate use of the apparatus 310 continuously, not just during overall manufacturing of a biological product, but simultaneous to, and continuous with, actual production of the biological product by a living system in the perfusion bioreactor 420.

For example, returning to FIG. 7, considering an apparatus 310 that is connected to a perfusion bioreactor 420 via the initial-mixing vessel 320, e.g. directly or indirectly, during operation of the perfusion bioreactor 420, such that a composition including a biological product flows from the perfusion bioreactor 420 to the initial-mixing vessel 320 without first being subjected to a processing step, such as filtration, precipitation, and/or chromatographic separation, wherein the perfusion bioreactor 420 has a working volume 422 in the range of 100 L to 2000 L and is being operated at a rate of 2 L to 160 L per hour, the internal volume 342 of the pre-treatment hold reservoir 340 can be 25 mL to 14 L, and the internal volume 212 of the treatment vessel 210 can be 8 L to 250 L. Moreover, in some examples wherein the perfusion bioreactor 420 has a working volume 422 of 100 L and is being operated at a rate of 2 L to 8 L per hour, the internal volume 342 of the pre-treatment hold reservoir 340 can be 25 mL to 700 mL, e.g. 30 mL to 140 mL, and the internal volume 212 of the treatment vessel 210 can be 8 L to 20 L, e.g. 9 L to 15 L. Moreover, in some examples wherein the perfusion bioreactor 420 has a working volume 422 of 500 L and is being operated at a rate of 10 L to 40 L per hour, the internal volume 342 of the pre-treatment hold reservoir 340 can be 160 mL to 3.5 L, e.g. 180 mL to 700 mL, and the internal volume 212 of the treatment vessel 210 can be 10 L to 60 L, e.g. 11 L to 46 L. Moreover, in some examples wherein the perfusion bioreactor 420 has a working volume 422 of 2000 L and is being operated at a rate of 40 L to 160 L per hour, the internal volume 342 of the pre-treatment hold reservoir 340 can be 600 mL to 14 L, e.g.

700 mL to 2.8 L, and the internal volume 212 of the treatment vessel 210 can be 44 L to 250 L, e.g. 46 L to 180 L.

Also for example, returning to FIG. 8, considering an apparatus 310 that is connected to a perfusion bioreactor 420 via the initial-mixing vessel 320, indirectly, during operation thereof, such that a composition including a biological product flows from the perfusion bioreactor 420 to a chromatography column 520 including a chromatography matrix 524, is subjected to chromatographic separation, and then flows to the initial-mixing vessel 320, the internal volume 522 of the chromatography column 520 can be about 100-fold less than the a working 422 of the perfusion bioreactor 420. Moreover, the internal volume 342 of the pre-treatment hold reservoir 340 and the internal volume 212 of the treatment vessel 210 can be scaled down 10-fold to 40-fold, given that the biological product will be more highly concentrated. Thus, in some examples wherein the perfusion bioreactor 420 has a working volume 422 in the range of 100 L to 2000 L and is being operated at a rate of 2 L to 160 L per hour, and further wherein the chromatography column 520 has an internal volume 522 of 1 L to 20 L, the internal volume 342 of the pre-treatment hold reservoir 340 can be 0.63 mL to 1.4 L, and the internal volume 212 of the treatment vessel 210 can be 200 mL to 25 L. Moreover, in some examples wherein the perfusion bioreactor 420 has a working volume 422 of 100 L and is being operated at a rate of 2 L to 8 L per hour, and further wherein the chromatography column 520 has an internal volume 522 of 1 L, the internal volume 342 of the pre-treatment hold reservoir 340 can be 0.63 mL to 70 mL, e.g. 0.75 mL to 14 mL, and the internal volume 212 of the treatment vessel 210 can be 200 mL to 2 L, e.g. 230 mL to 1.5 L. Moreover, in some examples wherein the perfusion bioreactor 420 has a working volume 422 of 500 L and is being operated at a rate of 10 L to 40 L per hour, and further wherein the chromatography column 520 has an internal volume 522 of 5 L, the internal volume 342 of the pre-treatment hold reservoir 340 can be 4 mL to 350 mL, e.g. 4.5 mL to 70 mL, and the internal volume 212 of the treatment vessel 210 can be 250 mL to 6 L, e.g. 280 mL to 4.6 L. Moreover, in some examples wherein the perfusion bioreactor 420 has a working volume 422 of 2000 L and is being operated at a rate of 40 L to 160 L per hour, and further wherein the chromatography column 520 has an internal volume 522 of 20 L, the internal volume 342 of the pre-treatment hold reservoir 340 can be 15 mL to 1.4 L, e.g. 17.5 mL to 280 mL, and the internal volume 212 of the treatment vessel 210 can be 1.1 L to 25 L, e.g. 1.2 L to 18 L. As noted above, the pre-treatment detector chamber 330 can be, for example, a chamber in which a pH probe, conductivity probe, or temperature probe is in contact with the treatment composition, or a chamber in which the treatment composition can be subjected to spectrophotometric or spectroscopic analysis. As shown in FIG. 5, the apparatus 310 can further include a pre-treatment detector 335 attached thereto, e.g. attached to the pre-treatment detector chamber 330. The pre-treatment detector 335 can be, for example, a pH meter, a conductivity meter, a temperature meter, a spectrophotometric device, a spectroscopic device, that can be used to measure a characteristic of the treatment composition as the composition flows through the pre-treatment detector chamber 330. This can be useful, for example, to determine a characteristic of the treatment composition, such as pH, conductivity, a temperature, a spectrophotometric characteristic, a spectroscopic characteristic, toward confirming that the treatment composition has a predetermined property, as discussed above.

As shown in FIG. 5, the apparatus 310 can further include a pre-combination detector chamber 360, fluidically connected to the initial-mixing vessel 320, e.g. directly or indirectly, through which the composition including the biological product flows prior to being added to the initial-mixing vessel 320. The pre-combination detector chamber 360 can be, for example, a chamber in which a pH probe, conductivity probe, or temperature probe is in contact with the composition including the biological product, or a chamber in which the composition including the biological product can be subjected to spectrophotometric or spectroscopic analysis. Moreover, the apparatus 310 can further include a pre-combination detector 365 attached thereto, e.g. attached to the pre-combination detector chamber 360. The pre-combination detector 365 can be, for example, a pH meter, a conductivity meter, a temperature meter, a spectrophotometric device, a spectroscopic device that can be used to measure a characteristic of the composition including the biological product as the composition flows through the pre-combination detector chamber 360. This can be useful, for example, to provide a baseline for comparison with a characteristic of a corresponding portion of the treatment composition, as determined by the pre-treatment detector 335, as discussed above.

In a third aspect of the disclosure, as shown in FIG. 1, with reference to FIG. 5, a method of use of the apparatus 310 for continuously inactivating a virus during manufacture of a biological product is provided. The method includes a step (1) 110 of combining, in the initial-mixing vessel 320, (a) a composition including a biological product, and (b) a composition including a virus-inactivation reagent, to obtain (c) a treatment composition having a predetermined property for inactivation of a virus. The method also includes a step (2) 120 of confirming, as the treatment composition passes through the pre-treatment detector chamber 330, that the treatment composition exhibits the predetermined property. The method also includes a step (3) 130 of transferring, via the pre-treatment hold reservoir 340, the treatment composition to the treatment vessel 210, the transferring occurring at the inlet 220. The method also includes a step (4) 140 of incubating the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property. The method also includes a step (5) 150 of collecting the treatment composition from the treatment vessel 210 at the outlet 220. In accordance with the method, step (1) 110, step (2) 120, step (3) 130, step (4) 140, and step (5) 150 are carried out continuously.

The method of use of the apparatus 310 for continuously inactivating virus during manufacture of a biological product can be carried out as described above generally for the method for continuously inactivating virus during manufacture of a biological product. Thus, for example, the predetermined property of the treatment composition can include at least one of (a) a pH between 3.0 to 3.8 or (b) a detergent concentration between 0.05% and 10% (v/v). Also for example, the virus-inactivation reagent can include at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm.

Also for example, the virus-inactivation reagent can be an organic acid having a titratable group having a pKa between 2.3 to 4.2 and not having another titratable group having a pKa between 4.2 and 8.5, lactic acid, formic acid, ascorbic acid, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be an amino acid having a titratable group having a pKa between 2.3 to 4.2 and not having another titratable group having a pKa between 4.2 and 8.5, glycine, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be a polyethylene oxide detergent having an aromatic group, Triton-X 100 detergent, or a combination thereof, and the predetermined property of the treatment composition can include a detergent concentration between 0.05% and 10% (v/v). In accordance with this example, the confirming of step (2) 120 can include measuring ultraviolet absorption of the treatment composition, wherein the ultraviolet absorption indicates the concentration of the detergent in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition.

Also for example, the combination of the predetermined temperature and the predetermined rate can be sufficient to cause inactivation of the virus in the treatment composition by the virus-inactivation reagent during step (4) 140 by a factor of at least $1 \times 10^1$. Also for example, the predetermined temperature can be between 17 and 40° C. and the predetermined rate can be 0.3 to 3 times the internal volume 212 of the treatment vessel 210 per hour. Also for example, the internal volume 212 of the treatment vessel 210 can be sufficiently large to ensure that not more than one part per million of the treatment composition has a residence time in the treatment vessel of a shorter duration than that required to cause inactivation of the virus in the treatment composition by the virus-inactivation reagent during step (4) 140 by a factor of at least $1 \times 10^1$.

Also for example, step (1) 110, step (2) 120, step (3) 130, step (4) 140, and step (5) 150 can be carried out continuously for at least one hour. Also for example, step (1) 110, step (2) 120, step (3) 130, step (4) 140, and step (5) 150 can be carried out continuously, not just during overall manufacturing of the biological product, but simultaneous to, and continuous with, actual production of the biological product by a living system, e.g. during continuous cultivation in a perfusion bioreactor 420, during manufacture of the biological product. Also for example, if there is a failure to confirm that the treatment composition exhibits the predetermined property at step (2) 120, then a corresponding portion of the treatment composition can be diverted and thus not transferred during step (3) 130. Also for example, if there is a failure to confirm that the treatment composition exhibits the predetermined property at step (2) 120, then a corresponding portion of the treatment composition can be diverted and thus not collected during step (5) 150.

In a fourth aspect of the disclosure, as shown in FIG. 7, a system 410 for continuously inactivating a virus during manufacture of a biological product is provided. The system 410 includes a perfusion bioreactor 420 and an apparatus 310 for continuously inactivating virus during manufacture of a biological product.

In accordance with the system 410, the apparatus 310 includes an initial-mixing vessel 320, a pre-treatment detector chamber 330, a pre-treatment hold reservoir 340, a drain valve 350, and a treatment vessel 210. The treatment vessel 210 includes an inlet 220, an outlet 230, and a static mixer 240. The inlet 220 and the outlet 230 are positioned at opposite ends, i.e. an inlet end 250 and an outlet end 260, of a major axis 270 of the treatment vessel 210. The static mixer 240 is internal to the treatment vessel 210 along the major axis 270. The initial-mixing vessel 320, the pre-treatment detector chamber 330, the pre-treatment hold reservoir 340, and the treatment vessel 210 each have an internal volume, i.e. internal volumes 322, 332, 342, and 212, respectively, and are fluidically connected in series, e.g. directly or indirectly, such that a fluid can flow internally and at least unidirectionally from the initial-mixing vessel 320, to the pre-treatment detector chamber 330, then to the pre-treatment hold reservoir 340, and then to the treatment vessel 210. As shown in FIG. 5 and FIG. 6, respectively, the drain valve 350 is either connected to, and positioned between, the pre-treatment hold reservoir 340 and the inlet 220 of the treatment vessel 210, or connected to the outlet 230 of the treatment vessel 210. The ratio of the internal volume 342 of the pre-treatment hold reservoir 340 to the internal volume 212 of the treatment vessel 210 is 0.003 to 0.06.

As noted above, as shown in FIG. 5 and FIG. 6, respectively, the drain valve 350 is either connected to, and positioned between, the pre-treatment hold reservoir 340 and the inlet 220 of the treatment vessel 210, or connected to the outlet 230 of the treatment vessel 210. Again, the drain valve 350 can be used to divert the treatment composition, e.g. if there is a failure to confirm that the treatment composition exhibits a predetermined property.

As also noted above, the ratio of the internal volume 342 of the pre-treatment hold reservoir 340 to the internal volume 212 of the treatment vessel 210 is 0.003 to 0.06. Again, in accordance with this ratio, when the treatment vessel 210 is used to cause inactivation of the virus in the treatment composition, such that the predetermined temperature is between 17 and 40° C. and the predetermined rate is 0.3 to 3 times the internal volume 212 of the treatment vessel 210 per hour, then the residence time of the treatment composition in the pre-treatment hold reservoir 340 will be about 1 to 5 minutes.

Also in accordance with the system 410, the perfusion bioreactor 420 and the apparatus 310 are connected, e.g. directly or indirectly, via the initial-mixing vessel 320. Also, the perfusion bioreactor 420 has a working volume 422 that is 5 to 2400 fold greater than the internal volume of the treatment vessel.

For example, as shown in FIG. 7 and as discussed above, the apparatus 310 can be connected to a perfusion bioreactor 420 via the initial-mixing vessel 320, e.g. directly or indirectly, during operation of the perfusion bioreactor 420, such that a composition including a biological product flows from the perfusion bioreactor 420 to the initial-mixing vessel 320 without first being subjected to a processing step, such as filtration, precipitation, and/or chromatographic separation. In accordance with this example, the perfusion bioreactor 420 can have a working volume 422 that is 5 to 60 fold greater than the internal volume of the treatment vessel.

Also for example, as shown in FIG. 8 and as discussed above, the apparatus 310 can be connected to a perfusion bioreactor 420 via the initial-mixing vessel 320, indirectly, during operation thereof, such that a composition including a biological product flows from the perfusion bioreactor 420 to at least one processing device, e.g. a chromatography column 520 having an internal volume 522 and including a chromatography matrix 524, is subjected to a processing step, such as filtration, precipitation, and/or chromatographic separation, and then flows to the initial-mixing vessel 320. In accordance with this example, the perfusion bioreactor 420 can have a working volume 422 that is 50 to 2400 fold greater than the internal volume of the treatment vessel. Again, the chromatography matrix 524 can be, for example, a protein A antibody affinity chromatography matrix or an anion exchange chromatography matrix, among other suitable matrices.

As shown in FIG. 7 and FIG. 8, the system 410 also can further include a tank 430 for supplying the composition including the virus-inactivation reagent to the initial-mixing vessel 320. The tank 430 can be connected to the initial mixing vessel 320. The system 410 also can further include one or more pumps 440, e.g. positioned between the perfusion bioreactor 420 and/or the chromatography column 520 and the initial-mixing vessel 320, to control flow of the composition including the biological product to the apparatus 310, and/or positioned between the tank 430 and the initial-mixing vessel 320, to control flow of the composition including the virus-inactivation reagent to the initial-mixing vessel 320, among other positions. The one or more pumps 440 can be used to control relative flow rates of the composition including the biological product and the composition including the virus-inactivation reagent to the initial-mixing vessel 320, and thus to control the relative proportions of each used to prepare the treatment composition, and moreover can be used to control the flow rate of the treatment composition through the apparatus 310, to coordinate production of the biological product in the perfusion bioreactor 420 and inactivation of virus by use of the apparatus 310.

Figure 9:
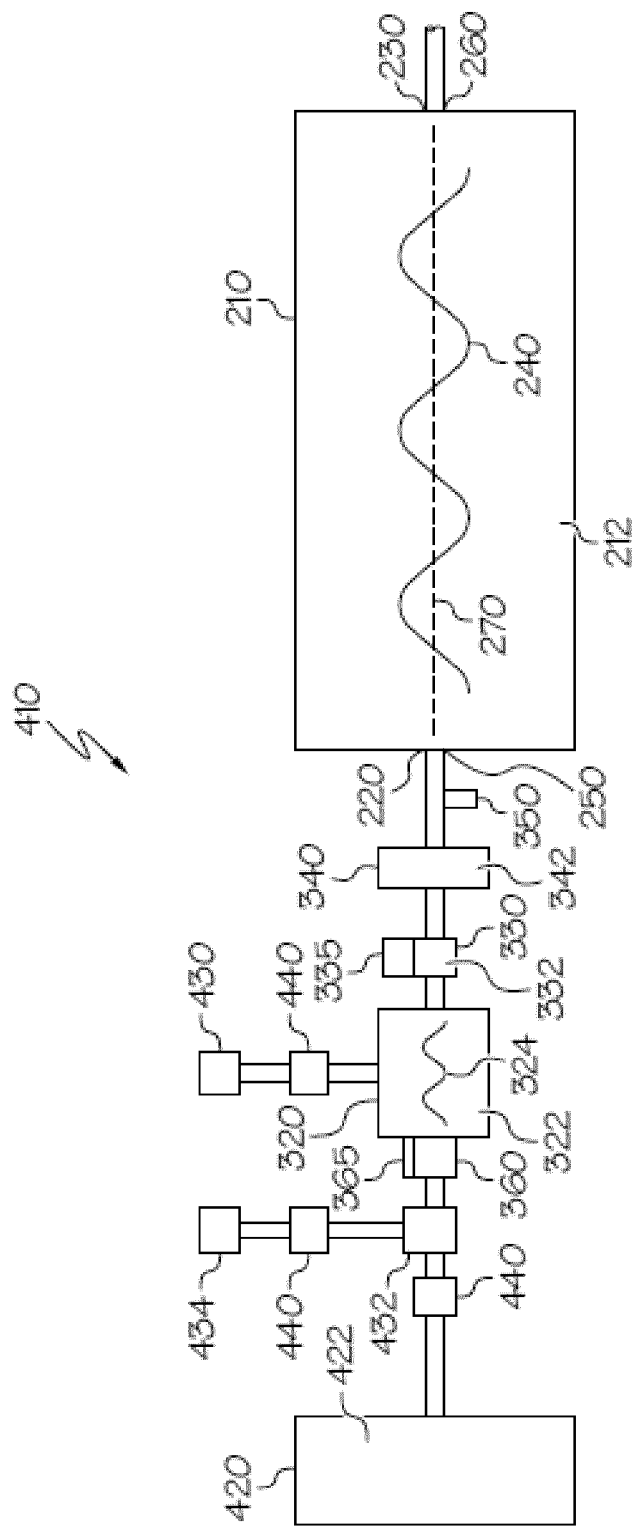
FIG. 9 is a schematic view of an example system 410 for continuously inactivating a virus during manufacture of a biological product, including a perfusion bioreactor 420 and the apparatus 310 of FIG. 5, and further including a pre-initial-mixing vessel 432 and a tank 434 for supplying a composition including a compound including a pH-sensitive group to the pre-initial-mixing vessel 432.
Figure 10:
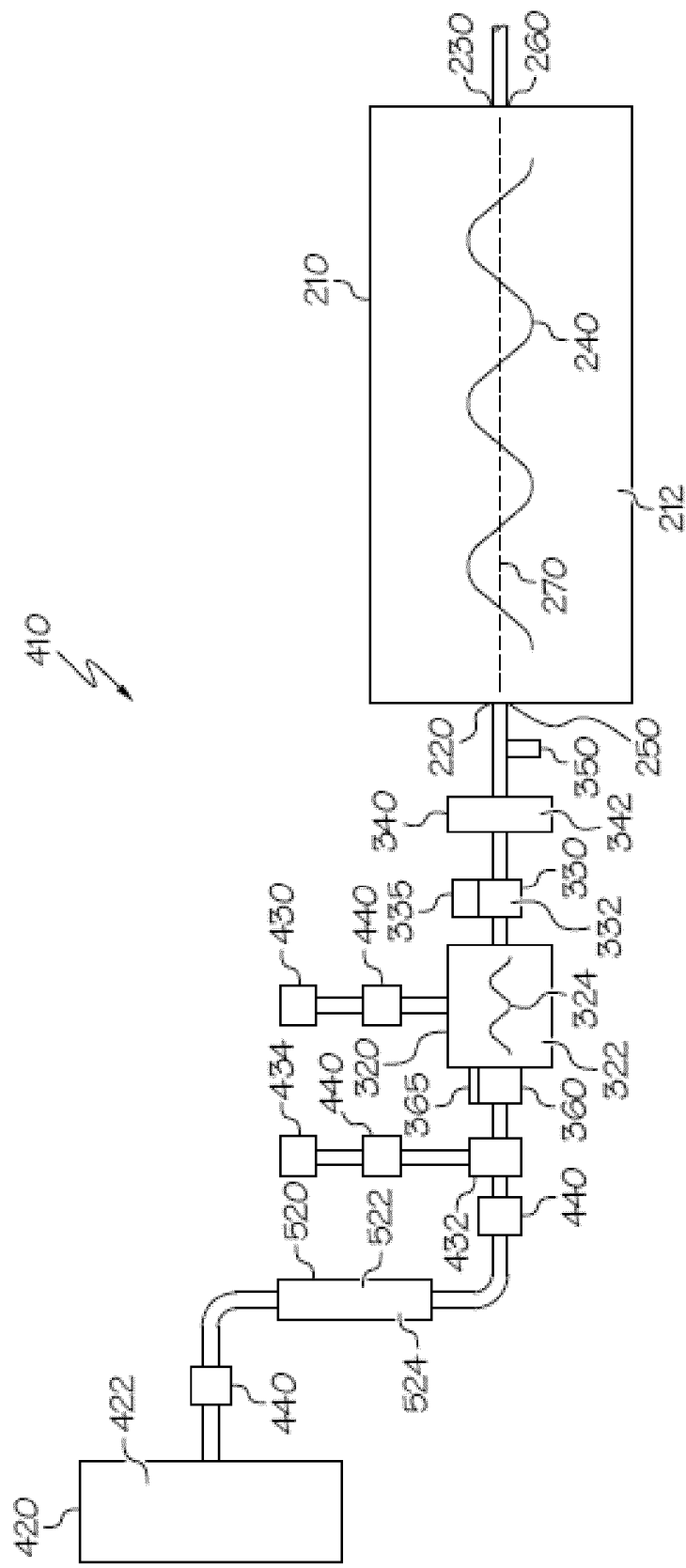
FIG. 10 is a schematic view of an example system 410 for continuously inactivating a virus during manufacture of a biological product, including a perfusion bioreactor 420, a chromatography column 520, and the apparatus 310 of FIG. 5, and further including a pre-initial-mixing vessel 432 and a tank 434 for supplying a composition including a compound including a pH-sensitive group to the pre-initial-mixing vessel 432.

As shown in FIG. 9 and FIG. 10, the system 410 also can further include a pre-initial-mixing vessel 432 and a tank 434 for supplying a composition including a compound including a pH-sensitive group to the pre-initial-mixing vessel 432. The compound including a pH-sensitive group can be a compound that is not included in the composition including the biological product as provided, but rather is subsequently added to the composition including the biological product, is included in the composition including the virus-inactivation reagent, and/or is otherwise added to the treatment composition, for measuring a spectroscopic characteristic of the treatment composition, e.g. an extrinsic chromophoric compound, wherein the spectroscopic characteristic indicates the pH of the treatment composition. The tank 434 can be connected to the pre-initial-mixing vessel 432. The system 410 also can further include one or more pumps 440, e.g. positioned between the perfusion bioreactor 420 and/or the chromatography column 520 and the pre-initial-mixing vessel 432, to control flow of the composition including the biological product to the apparatus 310, and/or positioned between the tank 434 and the pre-initial-mixing vessel 432, to control flow of the composition including a compound including a pH-sensitive group to the pre-initial-mixing vessel 432, among other positions. The one or more pumps 440 can be used to control relative flow rates of the composition including the biological product and the composition including a compound including a pH-sensitive group to the pre-initial-mixing vessel 432, and thus to control the relative proportions of each that will be used to prepare the treatment composition. For example, for a compound including a pH-sensitive group that is subsequently added to the composition including the biological product and is included in the composition including the virus-inactivation reagent, the one or more pumps 440 can be used to ensure that the treatment composition is prepared including the pH-sensitive group at a constant concentration, thus limiting variability of the spectroscopic characteristic of the treatment composition that might otherwise occur due to variation in the concentration of the pH sensitive group.

The apparatus 310 of the system 410, and the initial-mixing vessel 320, the pre-treatment detector chamber 330, the pre-treatment hold reservoir 340, the drain valve 350, and the treatment vessel 210 thereof can be like the apparatus 310, and the initial-mixing vessel 320, the pre-treatment detector chamber 330, the pre-treatment hold reservoir 340, the drain valve 350, and the treatment vessel 210 thereof, as described generally above. Thus, for example, the initial-mixing vessel 320 can be a vessel suitable for combining a composition including a biological product and a composition including a virus-inactivation reagent to obtain a treatment composition having a predetermined property for inactivation of a virus, as discussed above, and can include one or more initial mixers 324, as described above. Also for example, the pre-treatment detector chamber 330 can be, for example, a chamber in which a pH probe, conductivity probe, or temperature probe is in contact with the treatment composition, or a chamber in which the treatment composition can be subjected to spectrophotometric or spectroscopic analysis. Also for example, the pre-treatment hold reservoir 340 can be a reservoir suitable for allowing transfer of the treatment composition to the treatment vessel 210 at the inlet 220 to occur, for example, based on the treatment composition flowing under pressure from the pre-treatment detector chamber 330, as described above, to the treatment vessel 210, with pre-treatment hold reservoir 340 being fluidically connected to the pre-treatment detector chamber 330 and the treatment vessel 210, e.g. directly or indirectly, and positioned therebetween, as noted. Also for example, as shown in FIG. 2, the treatment vessel 210 can be in the form of, for example, a column or a tube, among other forms, as shown in FIG. 2, FIG. 3, and FIG. 4, respectively, the treatment vessel 210 can have a shape that is, for example, linear, curved, or spiral, among other shapes, and thus can have a major axis 270 that also is, for example, linear, curved, or spiral, among other types, and the treatment vessel 210 can be made from, for example, a metal, a plastic, or a combination thereof, among other materials. Also for example, as shown in FIG. 5, the treatment vessel 210 can be used to incubate the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property.

Also for example, the treatment composition can be collected from the treatment vessel 210 at the outlet 230.

The apparatus 310 can be configured for continuously inactivating virus during manufacture of a biological product, for example based on connection to the perfusion bioreactor 420, as discussed above. Moreover, the pre-treatment hold reservoir 340 and the treatment vessel 210 can be made or selected such that the respective internal volumes 342 and 212 thereof are dimensioned proportionally to a perfusion bioreactor 420 to which the apparatus 310 is connected and a perfusion rate at which the perfusion bioreactor 420 is being operated.

For example, returning to FIG. 7 and as discussed above, considering an apparatus 310 that is connected to a perfusion bioreactor 420 via the initial-mixing vessel 320, e.g. directly or indirectly, during operation of the perfusion bioreactor 420, such that a composition including a biological product flows from the perfusion bioreactor 420 to the initial-mixing vessel 320 without first being subjected to a processing step, such as filtration, precipitation, and/or chromatographic separation, wherein the perfusion bioreactor 420 has a working volume 422 in the range of 100 L to 2000 L and is being operated at a rate of 2 L to 160 L per hour, the internal volume 342 of the pre-treatment hold reservoir 340 can be 25 mL to 14 L, and the internal volume 212 of the treatment vessel 210 can be 8 L to 250 L. Moreover, in some examples wherein the perfusion bioreactor 420 has a working volume 422 of 100 L and is being operated at a rate of 2 L to 8 L per hour, the internal volume 342 of the pre-treatment hold reservoir 340 can be 25 mL to 700 mL, e.g. 30 mL to 140 mL, and the internal volume 212 of the treatment vessel 210 can be 8 L to 20 L, e.g. 9 L to 15 L. Moreover, in some examples wherein the perfusion bioreactor 420 has a working volume 422 of 500 L and is being operated at a rate of 10 L to 40 L per hour, the internal volume 342 of the pre-treatment hold reservoir 340 can be 160 mL to 3.5 L, e.g. 180 mL to 700 mL, and the internal volume 212 of the treatment vessel 210 can be 10 L to 60 L, e.g. 11 L to 46 L. Moreover, in some examples wherein the perfusion bioreactor 420 has a working volume 422 of 2000 L and is being operated at a rate of 40 L to 160 L per hour, the internal volume 342 of the pre-treatment hold reservoir 340 can be 600 mL to 14 L, e.g. 700 mL to 2.8 L, and the internal volume 212 of the treatment vessel 210 can be 44 L to 250 L, e.g. 46 L to 180 L.

Also for example, returning to FIG. 8 and as discussed above, considering an apparatus 310 that is connected to a perfusion bioreactor 420 via the initial-mixing vessel 320, indirectly, during operation thereof, such that a composition including a biological product flows from the perfusion bioreactor 420 to a chromatography column 520 including a chromatography matrix 524, is subjected to chromatographic separation, and then flows to the initial-mixing vessel 320, the internal volume 522 of the chromatography column 520 can be about 100-fold less than the working volume 422 of the perfusion bioreactor 420. Moreover, the internal volume 342 of the pre-treatment hold reservoir 340 and the internal volume 212 of the treatment vessel 210 can be scaled down 10-fold to 40-fold, given that the biological product will be more highly concentrated. Thus, in some examples wherein the perfusion bioreactor 420 has a working volume 422 in the range of 100 L to 2000 L and is being operated at a rate of 2 L to 160 L per hour, and further wherein the chromatography column 520 has an internal volume 522 of 1 L to 20 L, the internal volume 342 of the pre-treatment hold reservoir 340 can be 0.63 mL to 1.4 L, and the internal volume 212 of the treatment vessel 210 can be 200 mL to 25 L. Moreover, in some examples wherein the perfusion bioreactor 420 has a working volume 422 of 100 L and is being operated at a rate of 2 L to 8 L per hour, and further wherein the chromatography column 520 has an internal volume 522 of 1 L, the internal volume 342 of the pre-treatment hold reservoir 340 can be 0.63 mL to 70 mL, e.g. 0.75 mL to 14 mL, and the internal volume 212 of the treatment vessel 210 can be 200 mL to 2 L, e.g. 230 mL to 1.5 L. Moreover, in some examples wherein the perfusion bioreactor 420 has a working volume 422 of 500 L and is being operated at a rate of 10 L to 40 L per hour, and further wherein the chromatography column 520 has an internal volume 522 of 5 L, the internal volume 342 of the pre-treatment hold reservoir 340 can be 4 mL to 350 mL, e.g. 4.5 mL to 70 mL, and the internal volume 212 of the treatment vessel 210 can be 250 mL to 6 L, e.g. 280 mL to 4.6 L. Moreover, in some examples wherein the perfusion bioreactor 420 has a working volume 422 of 2000 L and is being operated at a rate of 40 L to 160 L per hour, and further wherein the chromatography column 520 has an internal volume 522 of 20 L, the internal volume 342 of the pre-treatment hold reservoir 340 can be 15 mL to 1.4 L, e.g. 17.5 mL to 280 mL, and the internal volume 212 of the treatment vessel 210 can be 1.1 L to 25 L, e.g. 1.2 L to 18 L.

Figure 11:
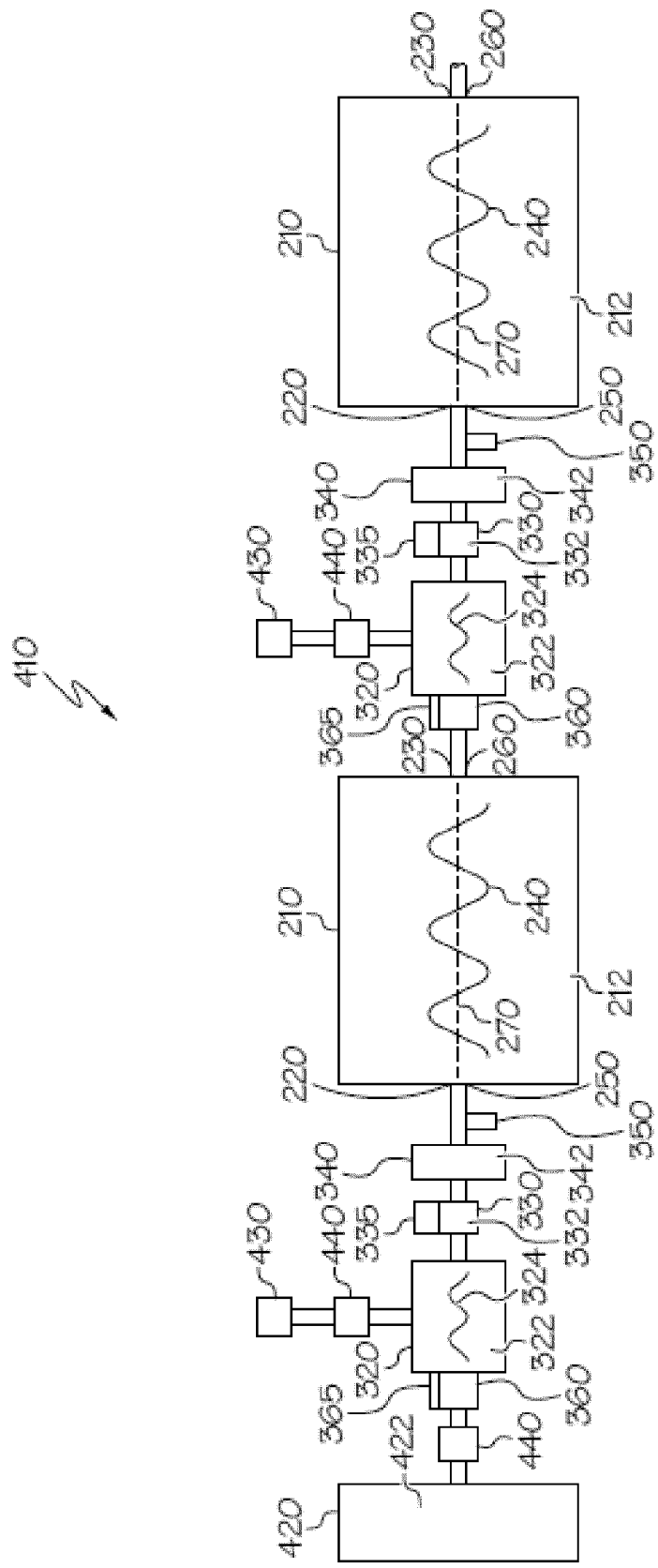
FIG. 11 is a schematic view of an example system 410 for continuously inactivating a virus during manufacture of a biological product, including two apparatuses 310 of FIG. 5, the first providing for inactivation of a virus by use of an organic acid, and the second providing for inactivation of a virus by use of a detergent.

The system 410 can include more than one apparatus 310, e.g. two apparatuses 310, three apparatuses 310, or more than three apparatuses 310. For example, as shown in FIG. 11, the system 410 can include two apparatuses 310, e.g. a first apparatus 310 for which the virus-inactivation reagent is an organic acid and/or an amino acid, as discussed above, and a second apparatus 310 for which the virus-inactivation reagent is a detergent, also as discussed above. Thus, the system 410 can be used to carry out two rounds of inactivation of virus, the first round corresponding to inactivation with an organic acid and/or an amino acid, and the second round corresponding to inactivation with a detergent. When carried out in this order, both rounds of inactivation of virus can be validated independently, particularly if the treatment composition is neutralized following the first round and prior to the second round, or if the composition including the virus-inactivation reagent to be used in the second round, i.e. the composition including the detergent, is also supplemented with base to neutralize the treatment composition. Moreover, when carried out in this order, the detergent to be used during the second round will not be present during the first round and thus will not interfere with validation of inactivation by the organic acid during the first round. Also for example, the system 410 also can include two apparatuses 310, e.g. a first apparatus 310 for which the virus-inactivation reagent is a detergent, and a second apparatus 310 for which the virus-inactivation reagent is an organic acid and/or an amino acid. Thus, the system 410 also can be used to carry out two rounds of inactivation of virus, the first round corresponding to inactivation with a detergent, and the second round corresponding to inactivation with an organic acid and/or an amino acid.

Returning to FIG. 8, as noted above, the apparatus 310 can be connected to a perfusion bioreactor 420 via the initial-mixing vessel 320, indirectly, during operation thereof, such that a composition including a biological product flows from the perfusion bioreactor 420 to at least one processing device, e.g. a chromatography column 520 having an internal volume 522 and including a chromatography matrix 524, is subjected to a processing step, such as filtration, precipitation, and/or chromatographic separation, and then flows to the initial-mixing vessel 320. In some examples in which the system 410 includes more than one apparatus 310, there are one or more processing devices, e.g. one or more chromatography columns 520, between the perfusion bioreactor 420 and the initial-mixing vessel 320. Alternatively or additionally, in some examples in which the system 410 includes more than one apparatus 310, there are one or more processing devices, e.g. one or more chromatography columns 520, between two or more apparatuses 310.

In a fifth aspect of the disclosure, as shown in FIG. 1, with reference to FIG. 7 and FIG. 8, a method of use of the system 410 for continuously inactivating a virus during manufacture of a biological product is provided. The method includes a step (0) 610 of transferring, from the perfusion bioreactor 420 to the apparatus 310 via the initial mixing vessel 320, e.g. directly or indirectly, a composition including a biological product. The method also includes a step (1) 110 of combining, in the initial-mixing vessel 320, (a) a composition including a biological product, and (b) a composition including a virus-inactivation reagent, to obtain (c) a treatment composition having a predetermined property for inactivation of a virus. The method also includes a step (2) 120 of confirming, as the treatment composition passes through the pre-treatment detector chamber 330, that the treatment composition exhibits the predetermined property. The method also includes a step (3) 130 of transferring, via the pre-treatment hold reservoir 340, the treatment composition to the treatment vessel 210, the transferring occurring at the inlet 220. The method also includes a step (4) 140 of incubating the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property. The method also includes a step (5) 150 of collecting the treatment composition from the treatment vessel 210 at the outlet 220. In accordance with the method, step (1) 110, step (2) 120, step (3) 130, step (4) 140, and step (5) 150 are carried out continuously.

The method of use of the system 410 for continuously inactivating virus during manufacture of a biological product can be carried out as described above generally for the method for continuously inactivating virus during manufacture of a biological product. Thus, for example, the predetermined property of the treatment composition can include at least one of (a) a pH between 3.0 to 3.8 or (b) a detergent concentration between 0.05% and 10% (v/v). Also for example, the virus-inactivation reagent can include at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm.

Also for example, the virus-inactivation reagent can be an organic acid having a titratable group having a pKa between 2.3 to 4.2 and not having another titratable group having a pKa between 4.2 and 8.5, lactic acid, formic acid, ascorbic acid, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be an amino acid having a titratable group having a pKa between 2.3 to 4.2 and not having another titratable group having a pKa between 4.2 and 8.5, glycine, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the biological product, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

Also for example, the virus-inactivation reagent can be a polyethylene oxide detergent having an aromatic group, Triton-X 100 detergent, or a combination thereof, and the predetermined property of the treatment composition can include a detergent concentration between 0.05% and 10% (v/v). In accordance with this example, the confirming of step (2) 120 can include measuring ultraviolet absorption of the treatment composition, wherein the ultraviolet absorption indicates the concentration of the detergent in the treatment composition. Alternatively or additionally, the confirming of step (2) 120 can include measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition.

Also for example, the combination of the predetermined temperature and the predetermined rate can be sufficient to cause inactivation of the virus in the treatment composition by the virus-inactivation reagent during step (4) 140 by a factor of at least $1 \times 10^1$. Also for example, the predetermined temperature can be between 17 and 40° C. and the predetermined rate can be 0.3 to 3 times the internal volume 212 of the treatment vessel 210 per hour. Also for example, the internal volume 212 of the treatment vessel 210 can be sufficiently large to ensure that not more than one part per million of the treatment composition has a residence time in the treatment vessel of a shorter duration than that required to cause inactivation of the virus in the treatment composition by the virus-inactivation reagent during step (4) by a factor of at least $1 \times 10^1$.

Also for example, step (1) 110, step (2) 120, step (3) 130, step (4) 140, and step (5) 150 can be carried out continuously for at least one hour. Also for example, step (1) 110, step (2) 120, step (3) 130, step (4) 140, and step (5) 150 can be carried out continuously, not just during overall manufacturing of the biological product, but simultaneous to, and continuous with, actual production of the biological product by a living system, e.g. during continuous cultivation in the perfusion bioreactor 420, during manufacture of the biological product. Also for example, if there is a failure to confirm that the treatment composition exhibits the predetermined property at step (2) 120, then a corresponding portion of the treatment composition can be diverted and thus not transferred during step (3) 130. Also for example, if there is a failure to confirm that the treatment composition exhibits the predetermined property at step (2) 120, then a corresponding portion of the treatment composition can be diverted and thus not collected during step (5) 150.

In a sixth aspect, a method for manufacturing a protein of interest is provided. The method includes a step (I) of cultivating a host cell in a culture medium with expression of a protein of interest by the host cell.

The protein of interest can be, for example, any of the proteins mentioned above, e.g. a therapeutic protein, such as an antibody, an antibody fragment, an antibody derivative, a cytokine, a growth factor, a hormone, an enzyme, or a blood coagulation factor, among others, or a vaccine protein, such as an antigenic protein, among others.

For example, the protein of interest can be an antibody, antibody fragment, or antibody derivative. Also for example, the antibody, antibody fragment, or antibody derivative can be selected from the group consisting of an antibody, a monoclonal antibody, a polyclonal antibody, a mammalian antibody, a murine antibody, a primate antibody, a human antibody, a chimeric antibody, a primatized antibody, a humanized antibody, an immunoglobulin light chain, an immunoglobulin heavy chain, an immunoglobulin light chain and an immunoglobulin heavy chain, an antibody fragment, an antibody derivative, an Fab fragment, an F(ab')$_2$ fragment, an Fc fragment, an Fc-Fc fusion protein, an Fv fragment, a single chain Fv fragment, a single domain Fv fragment, a tetravalent single chain Fv fragment, a disulfide-linked Fv fragment, a diabody, a triabody, a tetrabody, a pentabody, a minibody, a miniantibody, an immunoglobulin single variable domain, an immunoglobulin single variable heavy domain, an immunoglobulin single variable light domain, a VHH domain, a humanized VHH domain, a single-domain antibody, a protein including an immunoglobulin single variable domain linked together in a modular format with another immunoglobulin single variable domain or a functional domain, a multivalent protein including two or more of the same immunoglobulin single variable domain linked together in a modular format, a biparatopic protein including two different immunoglobulin single variable domains linked together in a modular format, a bispecific protein including two different immunoglobulin single variable domains linked together in a modular format, a bifunctional protein including an immunoglobulin single variable domain and a functional domain linked together in a modular format, a domain-deleted antibody, a fusion polypeptide of an antibody fragment with another peptide or polypeptide, an Fc-peptide fusion, an Fc-toxin fusion, and a fusion of an antibody fragment and a scaffold protein.

As is well known in the art, antibodies are proteins that bind specifically to particular substrates, i.e. their antigens, with antibodies generally sharing a similar overall structure, i.e. an immunoglobulin structure, and with each particular antibody molecule having a unique structure that allows the particular antibody to bind specifically to its corresponding antigen. Exemplary antibodies are described, for example, by Murphy et al., Janeway's Immunobiology, 7th edition, Garland Science, New York (2008). As is also well known, an antibody can correspond to a monoclonal antibody or a polyclonal antibody, depending on how the antibody has been generated, can correspond to a mammalian antibody, a murine antibody, a primate antibody, or a human antibody, depending on the organism from the which the antibody was, or could have been, derived, can correspond to a chimeric antibody, a primatized antibody, or a humanized antibody, depending on whether the antibody has been modified toward making the antibody more suitable for use in a particular organism, and can correspond to an immunoglobulin light chain, an immunoglobulin heavy chain, or an immunoglobulin light chain and an immunoglobulin heavy chain, among others, depending on the structure of the antibody, as described, for example, by Tamashiro et al., Monoclonal Antibodies, pp. 409-433, in Animal Cell Technology: From Biopharmaceuticals to Gene Therapy (eds. Castilho et al.), Taylor & Francis Group, New York (2008), among others. As is also well known, antibody fragments and antibody derivatives can be prepared from antibodies. For example, an Fab fragment (also termed fragment antigen-binding) consists of the variable regions of each of an immunoglobulin heavy chain and an immunoglobulin light chain, which are held together by adjacent constant regions. An Fab fragment may be formed by protease digestion, e.g. with papain, from conventional antibodies, or by genetic engineering. Similarly, an F(ab')$_2$ fragment includes the variable regions of each of two heavy chains and two light chains, also held together by adjacent constant regions. An F(ab')$_2$ fragment may be prepared by proteolytic cleavage by pepsin.

Moreover, using genetic engineering methods it is possible to produce a shortened antibody fragment that consists only of the variable regions of the heavy chain (VH) and of the light chain (VL), termed an Fv fragment (also termed fragment variable). Since an Fv fragment lacks constant regions of an immunoglobulin heavy chain and immunoglobulin light chain, and thus lacks covalent bonding between cysteines thereof, an Fv fragment often would be stabilized. For example, it is advantageous to use a short peptide to link the variable regions of the heavy chain and the light chain to stabilize an Fv fragment. The short peptide can include, for example, 10 to 30 amino acids, preferably 15 amino acids. In this way, a single peptide strand is obtained consisting of VH and VL, linked by a peptide linker. An antibody protein of this kind is known as a single-chain-Fv (also termed scFv). Exemplary scFv-antibody proteins of this kind are described by Huston et al., Proceedings of the National Academy of Sciences USA 85:5879-5883 (1988).

In addition, in recent years various strategies have been developed for preparing scFvs as a multimeric derivative. This is intended to lead, in particular, to recombinant antibodies having improved pharmacokinetic and biodistribution properties, as well as increased binding avidity. In order to achieve multimerization of scFvs, the scFvs were prepared as fusion proteins with multimerization domains. The multimerization domains may be, for example, the CH3 region of an immunoglobulin G (also termed IgG) or a coiled coil structure (helix structure) such as Leucine-zipper domains. There are also strategies in which the interaction between the VH/VL regions of the scFv are used for the multimerization, e.g. diabodies, triabodies, and pentabodies, among others.

Thus, for example, a diabody is a bivalent homodimeric scFv derivative. The shortening of the linker in an scFv molecule to 5 to 10 amino acids leads to the formation of homodimers in which an inter-chain VH/VL-superimposition takes place. Diabodies may additionally be stabilized by the incorporation of disulfide bridges. Exemplary diabodies are described, for example, by Perisic et al., Structure 2:1217-1226 (1994).

Also for example, a triabody is a trivalent homotrimeric scFv derivative. ScFv derivatives wherein VH-VL are fused directly without a linker sequence lead to the formation of timers. Exemplary triabodies are described, for example, by Kortt et al., Protein Engineering 10:423-433 (1997).

Also for example, a minibody is a bivalent homodimeric scFv derivative. A minibody consists of a fusion protein which contains the CH3 region of an immunoglobulin, preferably IgG, most preferably IgG1, as the dimerization region that is connected to the scFv via a hinge region (e.g. also from IgG1) and a linker region. Exemplary minibody antibody proteins are described, for example, by Hu et al., Cancer Research 56:3055-3061 (1996). Also for example, a miniantibody is an scFv derivative that has a bi-, tri-, or tetravalent structure. Miniantibody multimerization is carried out by di-, tri-, or tetrameric coiled coil structures, as disclosed for example by Lovejoy et al., Science 259:1288-1293 (1993), Pack et al., Biotechnology 11:1271-1277 (1993), and Pack et al., Journal of Molecular Biology 246:28-34 (1995).

Antibody fragments and antibody derivatives also include, for example, an immunoglobulin single variable domain. An immunoglobulin single variable domain can be, for example, an immunoglobulin single variable heavy domain (also termed VH domain) or an immunoglobulin single variable light domain (also termed VL domain), as described by Ward et al., Nature 341:544-546 (1989). An immunoglobulin single variable domain also can be, for example, a VHH domain, as derived from camelid heavy chain antibodies, as described by Hamers-Casterman et al., Nature 363:446-448 (1993), preferably a humanized VHH domain. An immunoglobulin single variable domain also can be, for example, a single-domain antibody. An immunoglobulin single variable domain also can be, for example, a NANOBODY® (trademark owned by Ablynx N.V.) therapeutic protein including one immunoglobulin single variable domain.

Antibody fragments and antibody derivatives also include, for example, a protein including an immunoglobulin single variable domain linked together in a modular format with another immunoglobulin single variable domain or a functional domain. Examples of such proteins include a multivalent protein including two or more of the same immunoglobulin single variable domain, e.g. two or more of the same VHH domain, linked together in a modular format, a biparatopic protein including two different immunoglobulin single variable domains, e.g. two different VHH domains, linked together in a modular format, each recognizing a different epitope on the same antigen, and a bispecific protein including two different immunoglobulin single variable domains, e.g. two different VHH domains, linked together in a modular format, each recognizing a different antigen. Examples of such proteins also include a bi-functional protein including an immunoglobulin single variable domain and a functional domain linked together in a modular format. Examples also include NANOBODY® multivalent, biparatopic, bispecific, and bi-functional therapeutic proteins. Antibody fragments and antibody derivatives also include, for example, a fusion of an antibody fragment and a scaffold protein, i.e. a protein including an antibody fragment and a scaffold protein fused to form a single polypeptide chain. In this context, a scaffold protein can be any functional domain of another protein that has been coupled, e.g. by genetic cloning or by co-translational processes, with an antibody fragment.

Considering other types of proteins, the protein of interest also can be, for example, insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosis factor (TNF), such as TNF alpha and TNF beta, TNF gamma, TRAIL, or G-CSF, GM-CSF, M-CSF, MCP-1 or VEGF. The protein of interest also can be, for example, erythropoietin or any other hormone growth factor. The protein of interest also can be, for example, a DARPin.

The host cell can be, for example, any of the cells mentioned above, e.g. a mammalian cell, a plant cell, or a bacterial cell, among others. The host cell can be, for example, a hamster cell, such as a BHK21, BHK TK⁻, CHO, CHO-K1, CHO-DUKX, CHO-DUKX B1, or CHO-DG44 cell or a derivative/progeny of such a cell line. The host cell also can be, for example, a murine myeloma cell, e.g. an NSO and Sp2/0 cell or a derivative/progeny of such a cell line. The host cell also can be, for example, derivatives/progenies of those cells, other mammalian cells, including but not limited to human, mice, rat, monkey, and rodent cell lines, or other eukaryotic cells, including but not limited to yeast cells and insect cells. Exemplary host cells are described, for example, by Leo et al., Animal Cells: Basic Concepts, pp. 13-37, in Animal Cell Technology: From Biopharmaceuticals to Gene Therapy (eds. Castilho et al.), Taylor & Francis Group, New York (2008), among others.

The culture medium can be, for example, a commercially available medium, such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invitrogen), serum-free CHO Medium (Sigma), and protein-free CHO Medium (Sigma). Any of the media may be supplemented as necessary with a variety of compounds, examples of which include hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations. Exemplary culture media are described, for example, by Moraes et al., Culture Media for Animal Cells, pp. 111-128, in Animal Cell Technology: From Biopharmaceuticals to Gene Therapy (eds. Castilho et al.), Taylor & Francis Group, New York (2008), among others.

The expression of the protein of interest by the host cell can include transcription and/or translation, within the host cell, of a nucleic acid sequence encoding the protein of interest. The level of expression of the protein of interest may be determined, for example, on the basis of the amount of corresponding mRNA encoding the protein of interest that is present in the host cell, the amount of the protein of interest present in the host cell, or the amount of the protein of interest secreted from the host cell, among other approaches. For example, the corresponding mRNA can be quantitated by Northern blot hybridization, ribonuclease RNA protection, in situ hybridization to cellular RNA, or RT-PCR, among other approaches, as described by Sambrook et al., Molecular Cloning: A Laboratory Manual, 2d edition, New York, Cold Spring Laboratory Press (1989), and Ausubel et al., Current Protocols in Molecular Biology, (1987-2014), among others. Also for example, the amount of the protein of interest, as present in the host cell or as secreted therefrom, can be quantitated by various methods, e.g. by ELISA, by Western blotting, by radioimmunoassay, by immunoprecipitation, by assaying for the biological activity of the protein, by immunostaining of the protein followed by FACS analysis, or by homogeneous time-resolved fluorescence (HTRF) assays, among other approaches, again as described by Sambrook et al. (1989), and Ausubel et al. (1987-2014), among others.

In accordance with step (I), the cultivation of the host cell in the culture medium, with expression of the protein of interest by the host cell, can be carried out by any of the processes for producing a biological product mentioned above, for example a homogeneous process, e.g. suspension culture based on use of a stirred-tank bioreactor, air-lift bioreactor, or wave bioreactor, or a heterogeneous process, e.g. adherent culture based on a microcarrier-based system, a packed bed bioreactor, or a hollow-fiber bioreactor, as carried out in a discontinuous mode, e.g. batch cultivation or fed-batch cultivation, or in a continuous mode, e.g. continuous cultivation with perfusion, and as carried out at any suitable scale, e.g. laboratory, pilot, or production scale. Exemplary processes are described, for example, by Véliz et al., Bioreactors for Animal Cells, pp. 221-258, in Animal Cell Technology: From Biopharmaceuticals to Gene Therapy (eds. Castilho et al.), Taylor & Francis Group, New York (2008), among others.

The method also includes at least one step (II) of continuously inactivating a virus during manufacture of the protein of interest. Returning to FIG. 1 and FIG. 2, step (II) includes a step (1) 110 of combining (a) a composition including the protein of interest, and (b) a composition including a virus-inactivation reagent, to obtain (c) a treatment composition having a predetermined property for inactivation of a virus, as described above, with the biological product being the protein of interest. Step (II) also includes a step (2) 120 of confirming that the treatment composition exhibits the predetermined property. Step (II) also includes a step (3) 130 of transferring the treatment composition to a treatment vessel 210 that includes an inlet 220, an outlet 230, and a static mixer 240 and having an internal volume 212, the inlet 220 and the outlet 230 being positioned at opposite ends, i.e. an inlet end 250 and an outlet end 260, of a major axis 270 of the treatment vessel 210 and the static mixer 240 being internal to the treatment vessel 210 along the major axis 270, and the transferring occurring at the inlet 220. Step (II) also includes a step (4) 140 of incubating the treatment composition in the treatment vessel 210 at a predetermined temperature while the treatment composition flows along the major axis 270 at a predetermined rate and contacts the static mixer 240, the combination of the predetermined temperature and the predetermined rate being sufficient to cause inactivation of the virus in the treatment composition based on the predetermined property. Step (II) also includes a step (5) 150 of collecting the treatment composition from the treatment vessel 210 at the outlet 230.

In accordance with the method, step (1) 110, step (2) 120, step (3) 130, step (4) 140, and step (5) 150 are carried out continuously, i.e. each step is carried out simultaneously, on different portions of the composition including the protein of interest, the composition including the virus-inactivation reagent, and the treatment composition, for at least some period of time. For example, step (1) 110, step (2) 120, step (3) 130, step (4) 140, and step (5) 150 can be carried out continuously for at least one hour, for at least 4 hours, for at least 12 hours, for at least 24 hours, for at least 3 days, for at least 10 days, or for at least 30 days, among other amounts of time. Also for example, step (1) 110, step (2) 120, step (3) 130, step (4) 140, and step (5) 150 can be carried out continuously, not just during overall manufacturing of the protein of interest, but simultaneous to, and continuous with, the cultivation of step (I), i.e. the cultivation of the host cell in the culture medium with expression of the protein of interest by the host cell.

Step (II) can be carried out as described above generally for the method for continuously inactivating virus during manufacture of a biological product. Thus, for example, the predetermined property of the treatment composition can include at least one of (a) a pH between 3.0 to 3.8 or (b) a detergent concentration between 0.05% and 10% (v/v). Also for example, the virus-inactivation reagent can include at least one of (a) an acid having a titratable group having a pKa between 2.3 to 4.2 and not having another titratable group having a pKa between 4.2 and 8.5, or (b) a non-ionic detergent having a chromophoric group having an absorption peak between 230 nm and 600 nm.

Also for example, the virus-inactivation reagent can be an organic acid having a titratable group having a pKa between 2.3 to 4.2 and not having another titratable group having a pKa between 4.2 and 8.5, lactic acid, formic acid, ascorbic acid, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the protein of interest and temperature of the composition including the virus-inactivation reagent and indicates the relative proportions of the composition including the protein of interest and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the protein of interest, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the protein of interest as provided, is subsequently added to the composition including the protein of interest, is included in the composition including the virus-inactivation reagent, and/or is otherwise added to the treatment composition, and the spectroscopic characteristic indicates the pH of the treatment composition.

Also for example, the virus-inactivation reagent can be an amino acid having a titratable group having a pKa between 2.3 to 4.2 and not having another titratable group having a pKa between 4.2 and 8.5, glycine, or a combination thereof, and the predetermined property of the treatment composition can include a pH between 3.0 to 3.8. In accordance with this example, the confirming of step (2) 120 can include measuring conductivity of the treatment composition, wherein the composition including the virus-inactivation reagent further includes a salt at a predetermined ratio to the virus-inactivation reagent and the conductivity indicates the concentration of the salt in the treatment composition. Alternatively or additionally, the confirming of step (2) 120 can include measuring an initial temperature of the treatment composition, wherein the initial temperature of the treatment composition is determined by a difference in temperature of the composition including the protein of interest and temperature of the composition including the virus-inactivation reagent and indicates the relative proportions of the composition including the protein of interest and the composition including the virus-inactivation reagent in the treatment composition. Alternatively or additionally, the confirming of step (2) 120 can include measuring a spectrophotometric characteristic of the treatment composition, wherein the composition including the virus-inactivation reagent further includes a chromophoric compound at a predetermined ratio to the virus-inactivation reagent and the spectrophotometric characteristic indicates the concentration of the chromophoric compound in the treatment composition. Alternatively or additionally, the confirming of step (2) 120 can include measuring a spectroscopic characteristic of the treatment composition, wherein the composition including the protein of interest, as provided, includes a pH-sensitive group and the spectroscopic characteristic indicates the pH of the treatment composition. Alternatively or additionally, the confirming of step (2) 120 can include measuring a spectroscopic characteristic of the treatment composition, wherein a compound including a pH-sensitive group, that is not included in the composition including the protein of interest as provided, is subsequently added to the composition including the protein of interest, is included in the composition including the virus-inactivation reagent, and/or is otherwise added to the treatment composition, and the spectroscopic characteristic indicates the pH of the treatment composition.

Also for example, the virus-inactivation reagent can be a polyethylene oxide detergent having an aromatic group, Triton-X 100 detergent, or a combination thereof, and the predetermined property of the treatment composition can include a detergent concentration between 0.05% and 10% (v/v). In accordance with this example, the confirming of step (2) 120 can include measuring ultraviolet absorption of the treatment composition, wherein the ultraviolet absorption indicates the concentration of the detergent in the treatment composition. Alternatively or additionally, the confirming of step (2) 120 can include measuring an initial temperature of the treatment composition, wherein the initial temperature of the treatment composition is determined by a difference in temperature of the composition including the protein of interest and temperature of the composition including the virus-inactivation reagent and indicates the relative proportions of the composition including the protein of interest and the composition including the virus-inactivation reagent in the treatment composition.

Also for example, the combination of the predetermined temperature and the predetermined rate can be sufficient to cause inactivation of the virus in the treatment composition by the virus-inactivation reagent during step (4) 140 by a factor of at least $1\times10^1$. Also for example, the predetermined temperature can be between 17 and 40° C. and the predetermined rate can be 0.3 to 3 times the internal volume 212 of the treatment vessel 210 per hour. Also for example, the internal volume 212 of the treatment vessel 210 can be sufficiently large to ensure that not more than one part per million of the treatment composition has a residence time in the treatment vessel of a shorter duration than that required to cause inactivation of the virus in the treatment composition by the virus-inactivation reagent during step (4) by a factor of at least $1\times10^1$.

Also for example, if there is a failure to confirm that the treatment composition exhibits the predetermined property at step (2) 120, then a corresponding portion of the treatment composition can be diverted and thus not transferred during step (3) 130. Also for example, if there is a failure to confirm that the treatment composition exhibits the predetermined property at step (2) 120, then a corresponding portion of the treatment composition can be diverted and thus not collected during step (5) 150.

The method also includes a step (III) of recovering the protein of interest from the culture medium. The recovering of step (III) can be carried out, for example, by subjecting the culture medium to a processing step, such as filtration, precipitation, and/or chromatographic separation, also as discussed above, among other approaches, thereby obtaining a composition including the protein of interest as recovered. As will be appreciated, it will generally be desirable to obtain the protein of interest in a form outside of the host cell before recovering the protein of interest from the culture medium. This can be accomplished, for example, by expression of the protein of interest in a form that will be secreted from the host cell, such that a portion of the culture medium that includes the host cell following expression of the protein of interest during step (I) will already include the protein of interest in a secreted form, with the protein of interest thus being outside of the host cell, prior to the recovering of step (III). This also can be accomplished, for example, by disruption of the host cell as present in a portion of the culture medium during step (III), e.g. based on cell lysis by enzymatic degradation, chemical solubilization, or autolysis, and/or physical disruption by use of blade homogenizers, among other approaches, resulting in release of the protein of interest from the host cell in the portion of the culture medium, again with the protein of interest thus being outside of the host cell.

As noted, the method includes at least one step (II) of continuously inactivating a virus during manufacture of the protein of interest. For example, step (II) can be carried out between step (I) and step (III) and/or after step (III). Also for example, step (II) can be carried out one, two, three, four, or more times.

Thus, in some examples step (II) is carried only between step (I) and step (III). For example, the host cell can be cultivated in a culture medium, with expression of the protein of interest by the host cell and secretion of the protein of interest into the culture medium. A portion of the culture medium including the protein of interest can then be subjected to inactivation of virus continuously, e.g. as the cultivation continues, followed by recovery of the protein of interest from the culture medium, e.g. by column chromatography, thereby obtaining a composition including the protein of interest as recovered. In accordance with these examples, step (II) can be carried out one, two, three, four, or more times, between step (I) and step (III). This can be based, for example, on step (II) being halted during diversion of the treatment composition due to a failure to confirm that the treatment composition exhibits the predetermined property at step (2), followed by resumption of step (II), as discussed above. This can also be based, for example, on the method including two rounds of inactivation of virus, the first round corresponding to inactivation with an organic acid, and the second round corresponding to inactivation with a detergent, also as discussed above, both rounds being carried out between step (I) and step (III).

Also in some examples, step (II) is carried only after step (III). For example, the host cell can be cultivated in a culture medium, with expression of the protein of interest by the host cell and secretion of the protein of interest into the culture medium. The protein of interest can then be recovered from a portion of the culture medium, e.g. by column chromatography, thereby obtaining a composition including the protein of interest as recovered, followed by subjecting the composition including the protein of interest as recovered to inactivation of virus continuously, e.g. as the cultivation continues. In accordance with these examples, step (II) also can be carried out one, two, three, four, or more times, after step (III). Again, this can be based, for example, on step (II) being halted during diversion of the treatment composition due to a failure to confirm that the treatment composition exhibits the predetermined property at step (2), followed by resumption of step (II). This can also be based, for example, on the method including two rounds of inactivation of virus, the first round corresponding to inactivation with an organic acid, and the second round corresponding to inactivation with a detergent, both rounds being carried out after step (III). Also in some examples, step (II) is carried both between step (I) and step (III) and after step (III). For example, the host cell can be cultivated in a culture medium, with expression of the protein of interest by the host cell and secretion of the protein of interest into the culture medium, subjected to inactivation of virus, then recovery, then further inactivation of virus, with the inactivation of virus both before and after recovery of the protein again being carried out continuously, e.g. as the cultivation continues. In accordance with these examples, step (II) also can be carried out one, two, three, four, or more times, as needed, between step (I) and step (III), and also can be carried out one, two, three, four, or more times, as needed, after step (III), as discussed above.

Example 1

Figure 12:
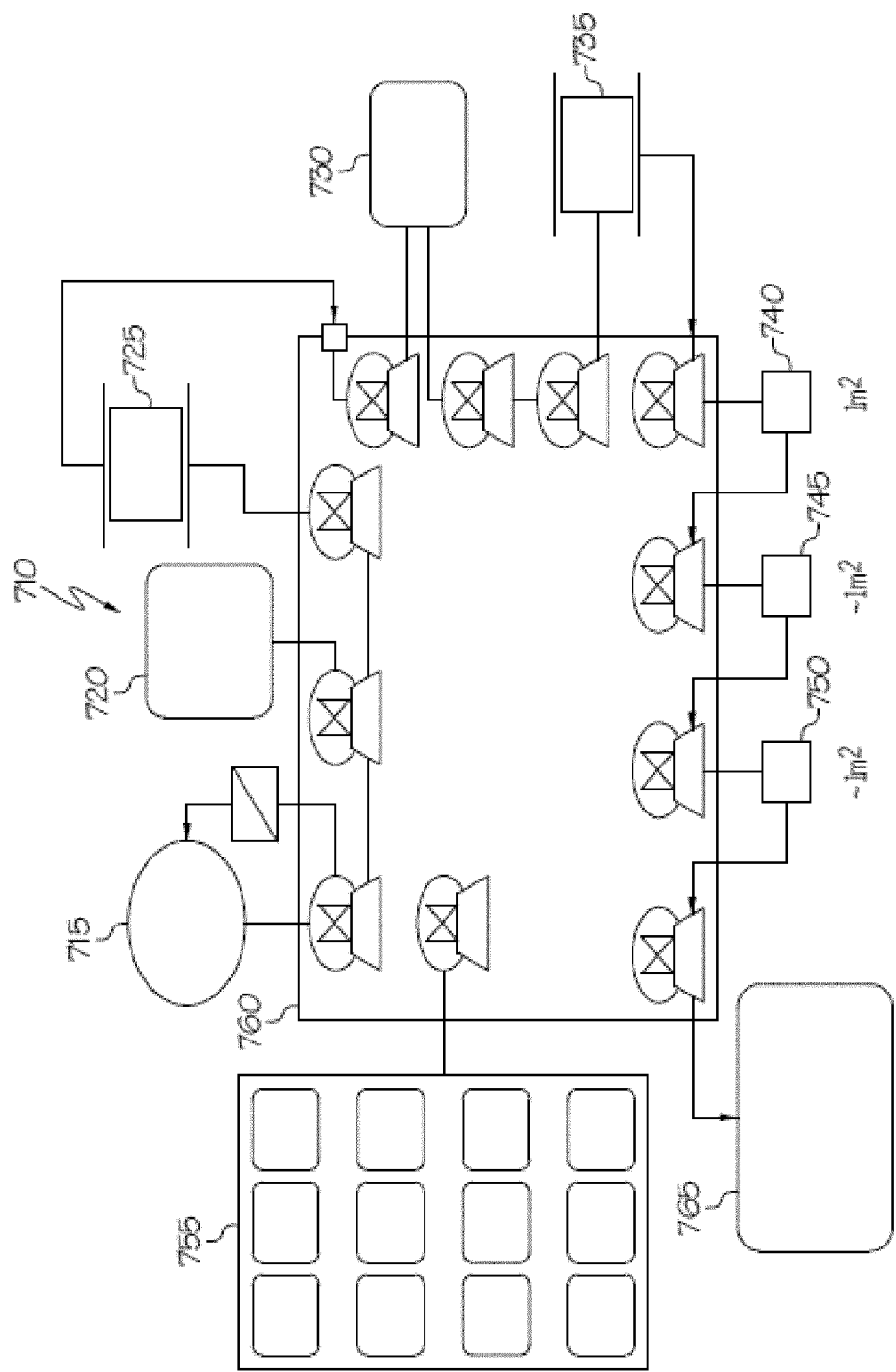
FIG. 12 is a schematic view of an example system 710 for continuously inactivating a virus during manufacture of a biological product (details: see Example 1)

An example system 710 for continuously inactivating a virus during manufacture of a biological product is shown in FIG. 12. The system 710 includes a 100 L perfusion bioreactor 715 (also termed "100 L BRX"), an apparatus 720 for continuously inactivating a virus by use of a detergent as described above (also termed "Detergnt Inactvn" or "detergent inactivation"), a device 725 for 1 L Protein A antibody affinity chromatography (also termed "1 L PrA"), a surge bag device 730 (also termed "Surge Bag"), a device 735 for 1 L anion exchange chromatography (also termed "1 L AEX"), a viral filtration device 740 (also termed "VRF"), an ultrafiltration device 745 (also termed "UF"), and a diafiltration device 750 (also termed "DF"), connected in series, with pumps and valve devices distributed therebetween. The system 710 is supplied by a solution farm 755 and is positioned on a skid 760. The system 710 can be used to produce about 30 to 80 kg of biological product 765 per year. The apparatus 720 for continuously inactivating a virus by use of a detergent can be used as described above. The system 710 also can be modified to further include an apparatus for continuously inactivating a virus by use of an organic acid ("acid inactivation"), also as described above, with that apparatus being connected in series with the others, and being positioned either (i) between the 100 L perfusion bioreactor and the detergent-inactivation apparatus, (ii) after the device for 1 L Protein A antibody affinity chromatography, (iii) before the viral filtration device, or (iv) after the viral filtration device.

In conventional methods for production of biological products, acid inactivation is carried out in a discontinuous mode, as a batch step, after a step of Protein A antibody affinity chromatography, which also is carried out in a discontinuous mode, as a batch step. In contrast, for continuous processing as disclosed here, it is preferred that acid-inactivation be carried out proximally to, i.e. in conjunction with, a continuous step. Thus, for example, since harvesting of culture from a perfusion bioreactor is carried out continuously, it is advantageous to carry out acid inactivation of virus proximally to the harvesting, and thus after the perfusion harvest and before any discontinuous step. Moreover, viral filtration, ultrafiltration, and diafiltration also can be carried out continuously, and if done so, it also would be advantageous to carry out the acid-inactivation proximally to the viral filtration, ultrafiltration, or diafiltration.

The methods, apparatuses, and systems for continuously inactivating a virus during manufacture of biological product can be used to coordinate production of a biological product in a bioreactor and inactivation of virus in compositions including the biological product. Use of a treatment vessel in accordance with the method as described ensures that a treatment composition having a predetermined property for inactivation of virus is subjected to treatment sufficient to accomplish inactivation of the virus to a desired extent, including accounting for, and minimizing, axial dispersion. Moreover, the overall configuration of the apparatuses and systems allows for diverse approaches for confirming that the treatment composition has the predetermined property, and for diverting a corresponding portion of the treatment composition if the treatment composition is not confirmed to have the predetermined property. In addition, use of an organic acid as described for inactivation of a virus allows for adequate buffering of a treatment composition without need for including high amounts of the organic acid, and allows for neutralization of the treatment composition without need for extra ions that would not otherwise be needed. Furthermore, carrying out two rounds of inactivation of virus, the first corresponding to inactivation with an organic acid, and the second step corresponding to inactivation with a detergent, allows for independent validation of both rounds of inactivation.

Example 2

Background

Accurate measurement of pH of a treatment composition corresponding to a product stream is required during methods for continuously inactivating a virus at low pH during manufacture of a biological product, initially to ensure that the pH of the product stream is lowered sufficiently, generally to a pH between 3.0 to 3.8, to inactivate viruses, and then to ensure that the pH of the treatment composition is raised sufficiently, generally to a pH between 5.0 and 8.5, to neutralize the product stream in preparation for subsequent purification steps. Regarding accuracy of measurement of pH in the lower range in particular, an accuracy of, for example, about 0.05 to 0.15 pH units, or about 0.10 pH units, is suitable.

One way to measure pH of a product stream is to use a common potentiometric pH probe. Such probes tend to drift in calibration and slow in response speed over time, though, both leading to error in pH measurement. Daily calibration with the probe in place can overcome calibration drift while maintaining the sterility of downstream operations, but it requires labor, time, can be mechanically complex, and is a potential source of error. Poor response speed is not as easily overcome. Thus, common potentiometric pH probes are not well suited for use with systems for continuous downstream processing.

An alternative way to measure pH of a product stream is to measure a spectral signal in the product stream that is pH-sensitive. If the spectral signal comes from a chromophoric compound already present in the product stream, e.g. in a composition including a biological product as provided, such as, for example, the biological product or a buffer, then the compound can be considered an intrinsic chromophoric compound. The use of an intrinsic chromophoric compound can be advantageous because the pH of the product stream can be measured spectrally without need for adding any extraneous compounds to the product stream. Alternatively or additionally, if the spectral signal comes from a chromophoric compound that is added to the product stream specifically to provide the spectral signal, e.g. the compound is not included in the composition including the biological product as provided, but rather is subsequently added to the composition including the biological product, is included in the composition including the virus-inactivation reagent, and/or is otherwise added to the treatment composition, then the compound can be considered an extrinsic chromophoric compound. Regarding extrinsic chromophoric compounds in particular, suitable extrinsic chromophoric compounds can be, for example, chemicals listed as FDA-approved GRAS substances and/or FDA-approved inactive ingredients. Use of extrinsic chromophoric compounds that are FDA-approved GRAS substances and/or FDA-approved inactive ingredients can be advantageous, based on minimizing risk to patients to whom the final drug product is administered. This is because even if the final drug product may contain trace amounts of the extrinsic chromophoric compound, the final drug product still will be safe for patients.

Figure 13:
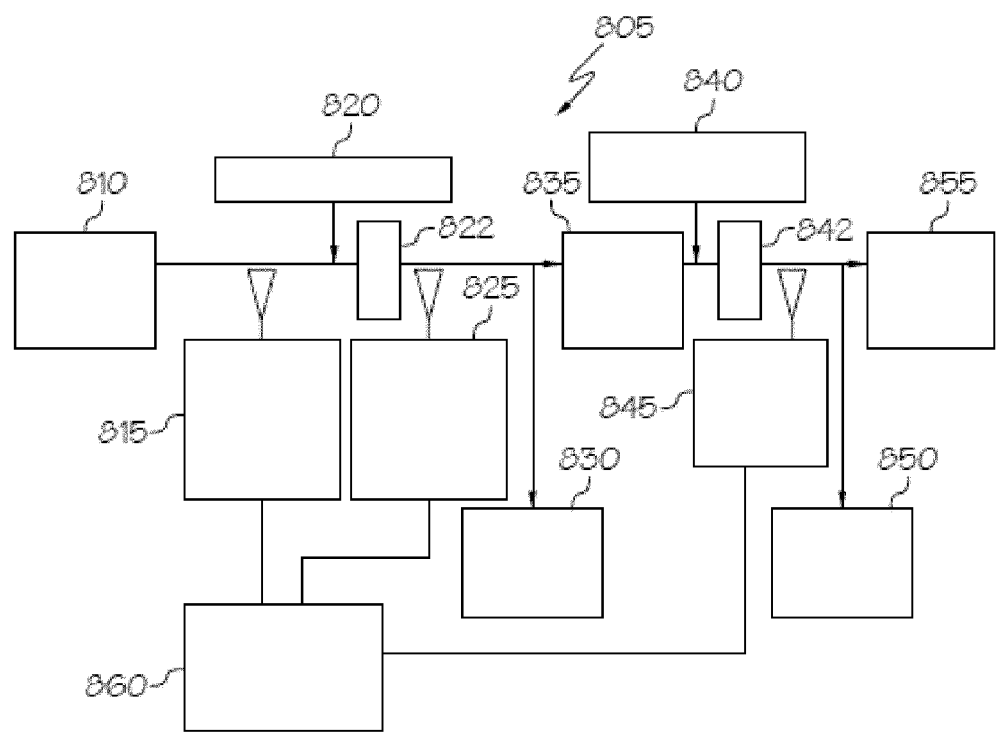
FIG. 13 is a process flow diagram of a method for continuously inactivating a virus at low pH during manufacture of a biological product, including measurement of a spectral signal of an intrinsic chromophoric compound to measure pH (details: see Example 2)

Experimental Evidence Demonstrating Feasibility of Spectral pH Measurement Using an Intrinsic Chromophoric Compound A process flow diagram 805 (also termed "PFD") of a method for continuously inactivating a virus at low pH during manufacture of a biological product, including measurement of a spectral signal of an intrinsic chromophoric compound to measure pH, is shown in FIG. 13. As shown, the process flow diagram 805 includes a step 810 of providing a product stream including a biological product from a bioreactor or purification column, a step 815 of use of a spectral probe to measure pH before addition of an inactivation acid, a step 820 of addition of the inactivation acid, a step 822 of mixing, a step 825 of use of a spectral probe to verify pH in range, a step 830 of diverting the product stream including the biological product if the pH is incorrect, a step 835 of treatment in a treatment vessel, a step 840 of adding a base for neutralization, a step 842 of mixing, a step 845 of use of a spectral probe to verify neutralization, a step 850 of diverting the product stream including the biological product if the pH is incorrect, one or more steps 855 of further processing, during which step 815, step 825, and step 845 are carried out based on a step 860 of computation of pH based on use of a computer with a multivariate model.

Figure 14:
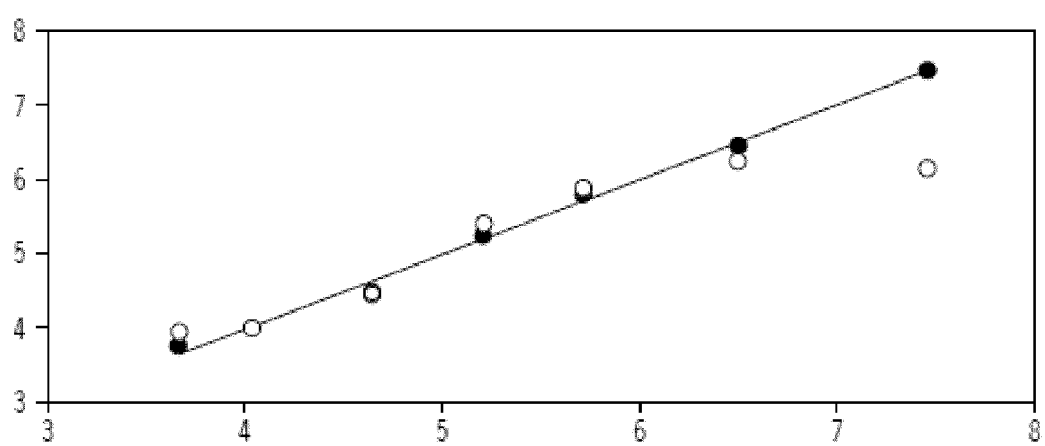
FIG. 14 is a plot of predicted pH (Y-axis) versus actual pH (X-axis), including "model pH" (solid circles), "cross-validation pH" (open circles), and a "target line" (solid line), for seven samples, based on fluorescence emission and multivariate data analysis (details: see TABLE 1 in Example 2)

Evidence demonstrating feasibility of using an intrinsic chromophoric compound for measurement of pH in this context is provided in TABLE 1 and FIG. 14.

TABLE 1

Preparation of samples for testing feasibility of use of an intrinsic chromophoric compound for measurement of pH.

| Sample | pH | 1 M Acetic acid (µL) | 1 M Tris base (µL) | Water to equalize volume (µL) | Total volume added (µL) |
|---|---|---|---|---|---|
| 1 | 3.67 | 750 | 0 | 0 | 750 |
| 2 | 4.04 | 200 | 0 | 550 | 750 |
| 3 | 4.65 | 30 | 0 | 720 | 750 |
| 4 | 5.21 | 20 | 0 | 730 | 750 |
| 5 | 5.72 | 7.5 | 0 | 742.5 | 750 |
| 6 | 6.50 | 0 | 12.5 | 742.5 | 755 |
| 7 | 7.47 | 0 | 30 | 720 | 750 |

Specifically, seven samples (10 mL each) of a buffered solution of monoclonal antibody typical of a composition exiting a Protein A antibody affinity chromatography column were pH-adjusted with 1 M acetic acid and 1 M tris base, then volumes of the samples were equalized with the addition of water, as described in TABLE 1. The volumes of the samples were equalized particularly to normalize concentrations of the monoclonal antibody, so that any spectral differences between samples were not due to differences in concentrations of the monoclonal antibody.

Fluorescence emission of each sample was then measured at 380 nm over 200-375 nm excitation (22° C.). UNSCRAMBLER® multivariate data analysis software, available from Camo (Oslo, Norway), was then used to test for correlation between fluorescence spectra and sample pH by the method of partial least squares (also termed "PLS"). Results are shown in FIG. 14, which is a plot of predicted pH (Y-axis) versus actual pH (X-axis), including "model pH" (solid circles), "cross-validation pH" (open circles), and a "target line" (solid line). In accordance with FIG. 14, the model pH measures how well the model fits experimental data ($R^2=0.997$), the cross-validation pH measures how well the model predicts experimental data ($R^2=0.861$), and the target line marks the points where there is perfect agreement between actual pH and predicted pH. The $R^2$ of 0.861 for the cross-validation pH shows that the model can predict pH reasonably well.

Figure 15:
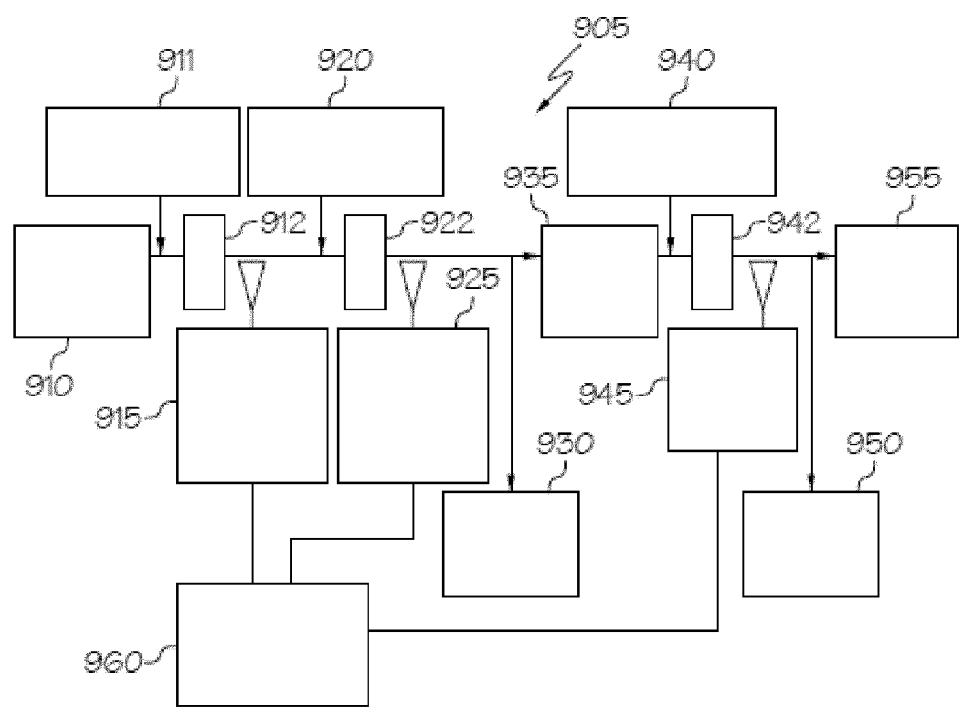
FIG. 15 is a process flow diagram of a method for continuously inactivating a virus at low pH during manufacture of a biological product, including measurement of a spectral signal of an extrinsic chromophoric compound to measure pH (details: see Example 2)

Experimental Evidence Demonstrating Feasibility of Spectral pH Measurement Using an Extrinsic Chromophoric Compound A process flow diagram 905 of a method for continuously inactivating a virus at low pH during manufacture of a biological product, including measurement of a spectral signal of an extrinsic chromophoric compound to measure pH, is shown in FIG. 15. As shown, the process flow diagram 905 includes a step 910 of providing a product stream including a biological product from a bioreactor or purification column, a step 911 of adding an extrinsic chromophoric compound, a step 912 of mixing, a step 915 of use of a spectral probe to measure pH before addition of an inactivation acid, a step 920 of addition of the inactivation acid, if needed, in combination with an extrinsic chromophoric compound, a step 922 of mixing, a step 925 of use of a spectral probe to verify pH in range, a step 930 of diverting the product stream including the biological product if the pH is incorrect, a step 935 of treatment in a treatment vessel, a step 940 of adding a base for neutralization in combination with an extrinsic chromophoric compound, a step 942 of mixing, a step 945 of use of a spectral probe to verify neutralization, a step 950 of diverting the product stream including the biological product if the pH is incorrect, one or more steps 955 of further processing, during which step 915, step 925, and step 945 are carried out based on a step 960 of computation of pH based on use of a computer with a multivariate model.

In accordance with this process flow diagram, initial pH of the product stream is measured. If the initial pH of the product stream is too high for virus inactivation, then inactivation acid is added. Alternatively, if the initial pH of the product stream is sufficiently low for virus inactivation, then inactivation acid is not added. Following addition of inactivation acid, if the pH of the product stream is inadequate, i.e. either too high or too low, then the product stream is diverted to waste. If the pH of the product stream is adequate, then the product stream is sent to the treatment vessel. After the product stream exits the treatment vessel, a neutralization solution is added to increase the pH to a level appropriate for subsequent steps in downstream processing. Following addition of the neutralization solution, if the pH of the product stream is inadequate, i.e. either too high or too low, then the product stream is diverted to waste. If the pH of the product stream is adequate, then the product stream is subjected to one or more steps of further processing.

As discussed, an extrinsic chromophoric compound is added to the product stream, in step 911. Moreover, an extrinsic chromophoric compound is included in a bulk solution of the inactivation acid, for addition in step 920. In addition, an extrinsic chromophoric compound is included in a bulk solution for neutralization, for addition in step 940.

The extrinsic chromophoric compounds added in step 911, step 920, and step 940 can be the same in one or more of the steps and/or can be different in one or more of the steps. For example, in accordance with one embodiment, the extrinsic chromophoric compound added in step 911, step 920, and step 940 can all be the same. Also for example, in accordance with another embodiment, the extrinsic chromophoric compound added in step 911 and step 920 can be a first extrinsic chromophoric compound, i.e. the same extrinsic chromophoric compound in both steps, such as an extrinsic chromophoric compound that exhibits a spectral signal useful for providing an accurate measure of pH within the range for inactivation of a virus at low pH. In accordance with this embodiment, the extrinsic chromophoric compound added in step 940 can be a second extrinsic chromophoric compound, i.e. different than the first extrinsic chromophoric compound, such as an extrinsic chromophoric compound that exhibits a spectral signal useful for providing an accurate measure of pH within the range for neutralization following inactivation of a virus at low pH and preceding further processing. Concentrations of the extrinsic chromophoric compounds can be equalized throughout the process flow diagram. For example, the extrinsic chromophoric compound included in the bulk solution of the inactivation acid, for addition in step 920, can be included at a concentration that is equal or approximately equal to that of the extrinsic chromophoric compound as present in the product stream. Similarly, the extrinsic chromophoric compound included in the bulk solution for neutralization, for addition in step 940, can be included at a concentration that is equal or approximately equal to that of the extrinsic chromophoric compound as present in the product stream. By so equalizing the concentrations of the extrinsic chromophoric compounds, an increase in accuracy of the multivariate model used to infer pH of the product stream from spectral measurements can be achieved.

Figure 16:
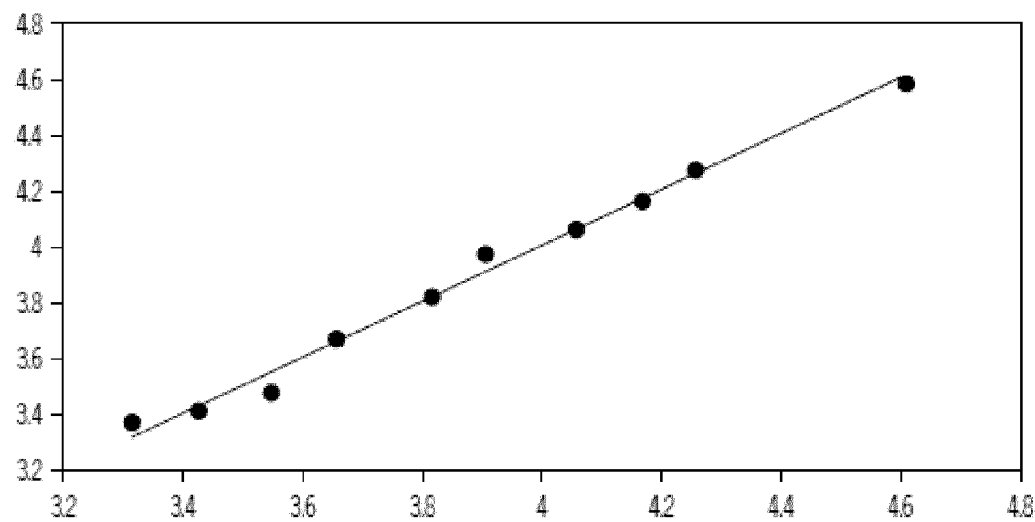
FIG. 16 is a plot of predicted pH (Y-axis) versus actual pH (X-axis), including "model pH" (solid circles) and a "target line" (solid line), for ten samples, based on UV/visible absorbance spectra and multivariate data analysis (details: see TABLE 2 in Example 2)

Evidence demonstrating feasibility of using an extrinsic chromophoric compound, specifically extrinsic chromophoric compounds corresponding to ascorbic acid and thiamine, for measurement of pH in this context is provided in TABLE 2 and FIG. 16.

TABLE 2

Results for testing feasibility of use of an extrinsic chromophoric compound for measurement of pH.

| Sample # | pH |
|---|---|
| 1 | 3.32 |
| 2 | 3.43 |
| 3 | 3.55 |
| 4 | 3.66 |
| 5 | 3.82 |
| 6 | 3.91 |
| 7 | 4.06 |
| 8 | 4.17 |
| 9 | 4.26 |
| 10 | 4.61 |

Specifically, ten samples (8 mL each) of a buffered solution of monoclonal antibody typical of a composition exiting a Protein A antibody affinity chromatography column were supplemented with solutions of concentrated ascorbic acid and thiamine. The solutions of concentrated ascorbic acid and thiamine were prepared including the same buffer composition as the buffered solution of monoclonal antibody, so that the resulting samples including ascorbic acid and thiamine would include a similar buffer composition. For each sample, pH was adjusted by addition of an inactivation composition, specifically 2 M glycine (pH 2.7), then volumes of the samples were equalized with the addition of the same buffer composition as the buffered solution of monoclonal antibody, as described in TABLE 2. Thus, all ten samples had equal concentrations of monoclonal antibody, ascorbic acid, and thiamine, and similar buffer compositions, so that any spectral differences between samples were not due to differences in concentrations of the monoclonal antibody, ascorbic acid, thiamine, or buffer composition.

UV/visible absorbance spectra of each sample was then obtained. A multivariate data analysis software program was used to test the correlation between the spectra and sample pH by the method of bootstrap re-sampling. Results are shown in FIG. 16, which is a plot of predicted pH (Y-axis) versus actual pH (X-axis), including "model pH" (solid circles) and a "target line" (solid line). The model pH shows how well the model fits the experimental data ($R^2$=0.991), and the target line marks the points where there is perfect agreement between actual pH and predicted pH. With 95% confidence, the model can predict pH within 0.104 pH units inside the modeled range of 3.3-4.5.

Figure 17:
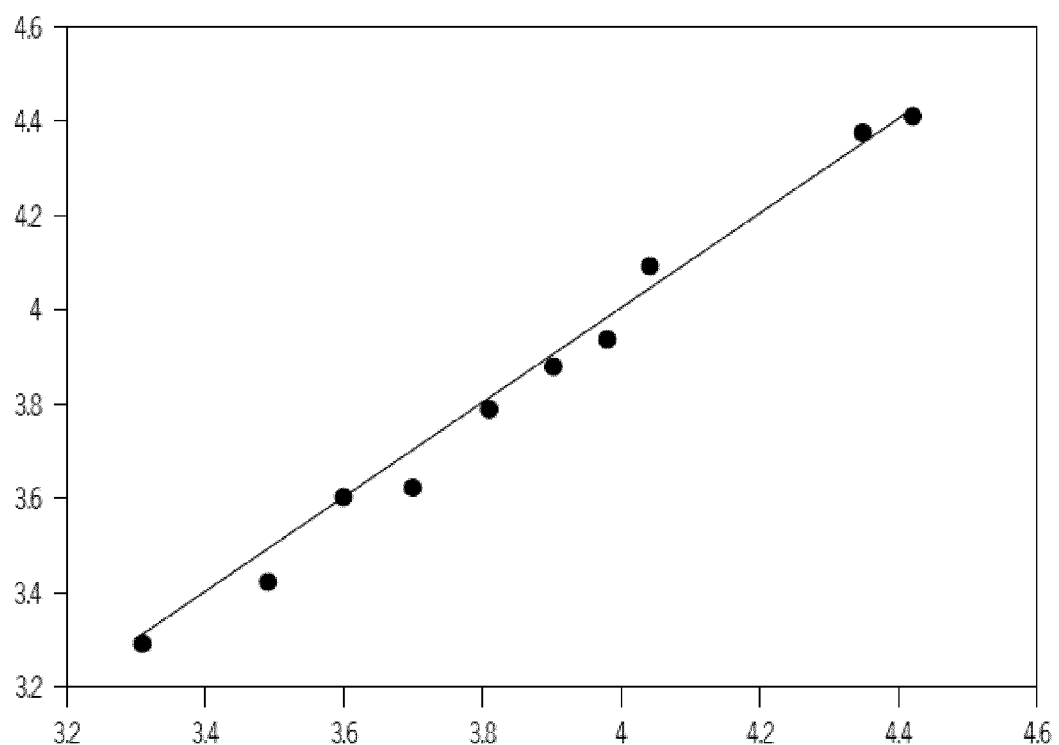
FIG. 17 is a plot of predicted pH (Y-axis) versus actual pH (X-axis), including "model pH" (solid circles) and a "target line" (solid line), for ten samples, based on UV/visible absorbance spectra and multivariate data analysis (details: see TABLE 3 in Example 2).

Further evidence demonstrating feasibility of using an extrinsic chromophoric compound, again extrinsic chromophoric compounds corresponding to ascorbic acid and thiamine, for measurement of pH is provided in TABLE 3 and FIG. 17.

TABLE 3

Further results for testing feasibility of use of an extrinsic chromophoric compound for measurement of pH.

| Sample # | Set 1 pH | Set 2 pH | Set 3 pH | Set 4 pH |
|---|---|---|---|---|
| 1 | 3.33 | 3.26 | 3.26 | 3.31 |
| 2 | 3.43 | 3.39 | 3.38 | 3.49 |
| 3 | 3.56 | 3.44 | 3.54 | 3.60 |
| 4 | 3.64 | 3.66 | 3.90 | 3.70 |
| 5 | 3.78 | 3.74 | 3.96 | 3.81 |
| 6 | 3.90 | 3.82 | 4.20 | 3.90 |
| 7 | 4.06 | 3.92 | 4.12 | 3.98 |
| 8 | 4.12 | 4.10 | 4.36 | 4.04 |
| 9 | 4.26 | 4.23 | 4.42 | 4.35 |
| 10 | 4.63 | 4.46 | 4.51 | 4.42 |

Specifically, four sample sets, each including ten samples (8 mL each) of a buffered solution of monoclonal antibody typical of a composition exiting a Protein A antibody affinity chromatography column were supplemented with solutions of concentrated ascorbic acid and thiamine, prepared as described above. Again, all samples had equal concentrations of monoclonal antibody, ascorbic acid, and thiamine, and similar buffer compositions, so that any spectral differences between samples were not due to differences in concentrations of the monoclonal antibody, ascorbic acid, thiamine, or buffer composition.

UV/visible absorbance spectra of each sample was then obtained. A multivariate data analysis software program was used to test the correlation between the spectra of sets 1-3 and sample pH by the method of bootstrap re-sampling. Results are shown in FIG. 17, which is a plot of predicted pH (Y-axis) versus actual pH (X-axis), including "model pH" (solid circles) and a "target line" (solid line). A six attribute model was formed showing an excellent correlation between predicted and actual pH ($R^2$=0.994). As shown in FIG. 17, the model was used to predict the pH of sample set 4 with an accuracy of ±0.07 pH units at the 95% confidence level. Predicting pH of samples of set 4 which were not used to generate the model is the strictest test of a model's quality, and is called external validation.

It will be apparent to those skilled in the art that various modifications and variations can be made to the described embodiments without departing from the spirit and scope of the claimed methods, apparatuses, and systems. Thus, it is intended that present claimed methods, apparatuses, and systems cover the modifications and variations of the embodiments described herein provided that they come within the scope of the appended claims and their equivalents.

INDUSTRIAL APPLICABILITY

The methods, apparatuses, and systems disclosed herein are useful for continuously inactivating a virus during manufacture of biological product, and thus for improving industrial methods for manufacturing biological products.

The invention claimed is:

1. A method for continuously inactivating a virus during manufacture of a biological product, the method comprising the steps of:
    (1) combining:
        (a) a composition comprising a biological product; and
        (b) a composition comprising a virus-inactivation reagent, to obtain:
        (c) a treatment composition having a predetermined property for inactivation of a virus;
    (2) confirming that the treatment composition exhibits the predetermined property;
    (3) transferring the treatment composition to a treatment vessel that comprises an inlet, an outlet, and a static mixer and having an internal volume, the inlet and the outlet being positioned at opposite ends of a major axis of the treatment vessel and the static mixer being internal to the treatment vessel along the major axis, and the transferring occurring at the inlet;
    (4) incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property; and
    (5) collecting the treatment composition from the treatment vessel at the outlet;
    wherein steps (1) to (5) are carried out continuously,
    wherein the predetermined property of the treatment composition comprises at least one of (a) a pH between 3.0 to 3.8 or (b) a detergent concentration between 0.05% and 10% (v/v), and wherein
        the virus-inactivation reagent is an organic acid having a titratable group having a pKa between 2.3 to 4.2 and not having another titratable group having a pKa between 4.2 and 8.5, lactic acid, formic acid, ascorbic acid, or a combination thereof; and
        the predetermined property of the treatment composition comprises a pH between 3.0 to 3.8, wherein the confirming of step (2) comprises at least one of:
    (a) measuring conductivity of the treatment composition, wherein the composition comprising the virus-inactivation reagent further comprises a salt at a predetermined ratio to the virus-inactivation reagent and the conductivity indicates the concentration of the salt in the treatment composition;
    (b) measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition;
    (c) measuring a spectrophotometric characteristic of the treatment composition, wherein the composition comprising the virus-inactivation reagent further comprises a chromophoric compound at a predetermined ratio to the virus-inactivation reagent and the spectrophotometric characteristic indicates the concentration of the chromophoric compound in the treatment composition;
    (d) measuring a spectroscopic characteristic of the treatment composition, wherein the composition comprising the biological product, as provided, comprises a pH-sensitive group and the spectroscopic characteristic indicates the pH of the treatment composition; or
    (e) measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

2. The method of claim 1, wherein:

the virus-inactivation reagent is an amino acid having a titratable group having a pKa between 2.3 to 4.2 and not having another titratable group having a pKa between 4.2 and 8.5, glycine, or a combination thereof; and the predetermined property of the treatment composition comprises a pH between 3.0 to 3.8, wherein the confirming of step (2) comprises at least one of:

(a) measuring conductivity of the treatment composition, wherein the composition comprising the virus-inactivation reagent further comprises a salt at a predetermined ratio to the virus-inactivation reagent and the conductivity indicates the concentration of the salt in the treatment composition;

(b) measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition;

(c) measuring a spectrophotometric characteristic of the treatment composition, wherein the composition comprising the virus-inactivation reagent further comprises a chromophoric compound at a predetermined ratio to the virus-inactivation reagent and the spectrophotometric characteristic indicates the concentration of the chromophoric compound in the treatment composition;

(d) measuring a spectroscopic characteristic of the treatment composition, wherein the composition comprising the biological product, as provided, comprises a pH-sensitive group and the spectroscopic characteristic indicates the pH of the treatment composition; or (e) measuring a spectroscopic characteristic of the treatment composition, wherein a compound including a pH-sensitive group, that is not included in the composition including the biological product as provided, is subsequently added to the composition including the biological product, is included in the composition including the virus-inactivation reagent, and/or is otherwise added to the treatment composition, and the spectroscopic characteristic indicates the pH of the treatment composition.

3. The method of claim 1, wherein the combination of the predetermined temperature and the predetermined rate is sufficient to cause inactivation of the virus in the treatment composition by the virus-inactivation reagent during step (4) by a factor of at least $1 \times 10^1$.

4. A method for continuously inactivating a virus during manufacture of a biological product, the method comprising the steps of:

(1) combining:
  (a) a composition comprising a biological product; and
  (b) a composition comprising a virus-inactivation reagent, to obtain:
  (c) a treatment composition having a predetermined property for inactivation of a virus;

(2) confirming that the treatment composition exhibits the predetermined property;

(3) transferring the treatment composition to a treatment vessel that comprises an inlet, an outlet, and a static mixer and having an internal volume, the inlet and the outlet being positioned at opposite ends of a major axis of the treatment vessel and the static mixer being internal to the treatment vessel along the major axis, and the transferring occurring at the inlet;

(4) incubating the treatment composition in the treatment vessel at a predetermined temperature while the treatment composition flows along the major axis at a predetermined rate and contacts the static mixer, the combination of the predetermined temperature and the predetermined rate being sufficient to cause inactivation of the virus in the treatment composition based on the predetermined property; and (5) collecting the treatment composition from the treatment vessel at the outlet;

wherein steps (1) to (5) are carried out continuously, wherein the predetermined property of the treatment composition comprises at least one of (a) a pH between 3.0 to 3.8 or (b) a detergent concentration between 0.05% and 10% (v/v), and wherein the virus-inactivation reagent is a non-ionic detergent having a chromophoric group having an absorption peak between 230 nm and 600 nm selected from the group consisting of a polyethylene oxide detergent having an aromatic group, polyoxyethylene octyl phenyl ether detergent, and combinations thereof, wherein:

the virus-inactivation reagent is a polyethylene oxide detergent having an aromatic group, polyoxyethylene octyl phenyl ether detergent, or a combination thereof; and the predetermined property of the treatment composition comprises a detergent concentration between 0.05% and 10% (v/v), wherein the confirming of step (2) comprises at least one of:

(a) measuring ultraviolet absorption of the treatment composition, wherein the ultraviolet absorption indicates the concentration of the detergent in the treatment composition; or (b) measuring an initial temperature of the treatment composition, wherein the initial temperature of the treatment composition is determined by a difference in temperature of the composition including the biological product and temperature of the composition including the virus-inactivation reagent and indicates the relative proportions of the composition including the biological product and the composition including the virus-inactivation reagent in the treatment composition.

* * * * *